US008057800B2

(12) United States Patent
O'Hehir et al.

(10) Patent No.: US 8,057,800 B2
(45) Date of Patent: Nov. 15, 2011

(54) IMMUNOINTERACTIVE MOLECULES AND USES THEREOF

(75) Inventors: Robyn O'Hehir, Melbourne (AU); Jennifer Rolland, Melbourne (AU)

(73) Assignee: Circassia Limited, Oxford (GB)

( * ) Notice: Subject to any disclaimer, the term of this patent is extended or adjusted under 35 U.S.C. 154(b) by 790 days.

(21) Appl. No.: 11/629,336

(22) PCT Filed: Jun. 10, 2005

(86) PCT No.: PCT/AU2005/000841
§ 371 (c)(1),
(2), (4) Date: Mar. 16, 2007

(87) PCT Pub. No.: WO2005/121166
PCT Pub. Date: Dec. 22, 2005

(65) Prior Publication Data
US 2008/0075725 A1 Mar. 27, 2008

(30) Foreign Application Priority Data

Jun. 10, 2004 (AU) .............................. 2004903184

(51) Int. Cl.
A61K 38/00 (2006.01)
A61K 39/00 (2006.01)
A61K 39/35 (2006.01)
A61K 39/36 (2006.01)
A01N 37/18 (2006.01)
C07K 1/00 (2006.01)
C07K 14/00 (2006.01)
C07K 17/00 (2006.01)

(52) U.S. Cl. .................. 424/185.1; 424/275.1; 435/810; 514/1.1; 530/350

(58) Field of Classification Search .................. None
See application file for complete search history.

(56) References Cited

U.S. PATENT DOCUMENTS

| 5,558,869 A | 9/1996 | Burks, Jr. et al. |
| 5,973,121 A | 10/1999 | Burks, Jr. et al. |
| 6,441,142 B1 | 8/2002 | Burks, Jr. et al. |
| 2003/0202980 A1 | 10/2003 | Caplan et al. |

FOREIGN PATENT DOCUMENTS

| WO | WO 97/24139 | | 7/1997 |
| WO | WO 99/38978 | | 8/1999 |
| WO | WO 99/45961 | | 9/1999 |
| WO | WO 00/51647 | * | 8/2000 |
| WO | WO 00/52154 | | 9/2000 |
| WO | WO 00/54803 | * | 9/2000 |
| WO | WO 01/36621 | A2 | 5/2001 |
| WO | WO 01/39799 | A2 | 6/2001 |
| WO | WO 01/40264 | A2 | 6/2001 |
| WO | WO 01/40264 | * | 7/2001 |
| WO | WO 03/037172 | A2 | 5/2003 |

OTHER PUBLICATIONS

Sen M. et al., "Protein Structure Plays a Critical Role in Peanut Allergen Stability and May Determine Immunodominant IgE-Binding Epitopes", The Journal of Immunology 169:882-887 (2002).
Burks A.W. et al., "Epitope Specificity of the Major Peanut Allergen, Ara h II", Journal of Allergy and Clinical Immunology 95:607-611 (1995).
Chatel J-M et al., "Isolation and Characterization of Two Complete Ara h 2 Isoforms cDNA", International Archives of Allergy and Immunology 131(1):14-18 (2003), together with STN FILE CA Abstract No. 139:379907.
Bayer K. et al., "Measurement of Peptide-Specific IgE as an Additional Tool in Identifying Patients With Clinical Reactivity to Peanuts", Journal of Allergy and Clinical Immunology 112(1)202-207 (2003), together with STN FILE CA Abstract No. 139:259597.
Viquez O.M. et al., "Isolation and Molecular Characterization of the First Genomic Clone of Major Peanut Allergen, Ara h 2", Journal of Allergy and Clinical Immunology 107(4):713-717 (2001), together with STN FILE CA Abstract No. 139:101378.
Li X-M et al., "A Murine Model of Peanut Anaphylaxis: T- and B-Cell Responses to a Major Peanut Allergen Mimic Human Responses", Journal of Allergy and Clinical Immunology 106(1, Pt 1):150-158 (2000), together with STN FILE CA Abstract No. 134:146305.
Kleber-Janke T. et al., "Use of Modified BL21 (DE3) Escherichia coli Cells for High-Level Expression of Recombinant Peanut Allergens Affected by Poor Condon Usage", Protein Expression and Purification 19(3):419-424 (2000), together with STN FILE CA Abstract No. 133:265668.
Stanley J.S. et al., "Identification and Mutational Analysis of the Immunodominant IgE Binding Epitopes of the Major Peanut Allergen Ara h 2", Archives of Biochemistry and Biophysics 342(2):244-253 (1997), together with STN FILE CA Abstract No. 127:120896.
Gruber P. et al., "Influence of the Maillard Reaction on the Allergenicity of rAra h 2, a Recombinant Major Allergen from Peanut (Arachis hypogaea), Its Major Epitopes, and Peanut Agglutinin", Journal of Agricultural and Food Chemistry 53(6):2289-2296 (2005), together with STN FILE CA Abstract No. 142:391170.
Glaspole I.N. et al., "Characterization of the T-Cell Epitopes of a Major Peanut Allergen, Ara h 2", Allergy 60:35-40 (2005).
Gruber P. et al., "Development of an Epitope-Specific Analytical Tool for the Major Peanut Allergen Ara h 2 Using a High-Density Multiple-Antigenic Peptide Strategy", Molecular Nutrition and Food Research 48(6):449-458 (2004), together with STN FILE CA Abstract No. 142:174809.

* cited by examiner

Primary Examiner — Nora Rooney
(74) Attorney, Agent, or Firm — Nelson Mullins Riley & Scarborough LLP; Jane E. Remillard, Esq.; Jeanne M. DiGiorgio, Esq.

(57) ABSTRACT

The present invention relates generally to molecules such as peptides, polypeptides and proteins which interact immunologically with T lymphocytes in subjects having peanut allergy, or allergy to other tree nuts, and genetic sequences encoding same. These molecules are preferentially immunointeractive with T cells in subjects having an allergy to the Ara h 2 allergen. The molecules of the present invention are useful in the development of diagnostic, therapeutic and prophylactic agents for conditions characterized by an aberrant, inappropriate or otherwise unwanted immune response to Ara h 2 or derivative or homologue thereof.

3 Claims, 10 Drawing Sheets

| | | | | | | | | | | | | | | | | | | | | | |
|---|---|---|---|---|---|---|---|---|---|---|---|---|---|---|---|---|---|---|---|---|---|
| SEQ ID NO: 2 | 1-20 | ¹L | T | I | L | V | A | L | A | L | F | L | L | A | A | H | A | S | A | R | Q²⁰ |
| SEQ ID NO: 3 | 10-29 | ¹⁰F | L | L | A | A | H | A | S | A | R | Q | Q | W | E | L | Q | G | D | R | R²⁹ |
| SEQ ID NO: 4 | 19-38 | ¹⁹R | Q | Q | W | E | L | Q | G | D | R | R | C | Q | S | Q | L | E | R | A | N³⁸ |
| SEQ ID NO: 5 | 28-47 | ²⁸R | R | C | Q | S | Q | L | E | R | A | N | L | R | P | C | E | Q | H | L | M⁴⁷ |
| SEQ ID NO: 6 | 37-56 | ³⁷A | N | L | R | P | C | E | Q | H | L | M | Q | K | I | Q | R | D | E | D | S⁵⁶ |
| SEQ ID NO: 7 | 46-65 | ⁴⁶L | M | Q | K | I | Q | R | D | E | D | S | Y | E | R | D | P | Y | S | P | S⁶⁵ |
| SEQ ID NO: 8 | 55-74 | ⁵⁵D | S | Y | E | R | D | P | Y | S | P | S | Q | D | P | Y | S | P | S | P | Y⁷⁴ |
| SEQ ID NO: 9 | 64-83 | ⁶⁴P | S | P | S | Q | D | P | Y | S | P | S | P | Y | D | R | R | G | A | G | S⁸³ |
| SEQ ID NO: 10 | 73-92 | ⁷³P | Y | D | R | R | G | A | G | S | S | S | Q | H | Q | E | R | C | C | N | E | L⁹² |
| SEQ ID NO: 11 | 82-101 | ⁸²S | S | Q | H | Q | E | R | C | C | N | E | L | N | E | F | E | N | N | Q | R | C¹⁰¹ |
| SEQ ID NO: 12 | 91-110 | ⁹¹E | L | N | E | F | E | N | N | Q | R | C | M | C | E | A | L | Q | Q | I | M¹¹⁰ |
| SEQ ID NO: 13 | 100-119 | ¹⁰⁰R | C | M | C | E | A | L | Q | Q | I | M | E | N | Q | S | D | R | L | Q | G¹¹⁹ |
| SEQ ID NO: 14 | 109-128 | ¹⁰⁹I | M | E | N | Q | S | D | R | L | Q | G | R | Q | Q | E | Q | Q | Q | C¹²⁸ |
| SEQ ID NO: 15 | 118-137 | ¹¹⁸Q | G | R | Q | Q | E | Q | Q | Q | C | Q | Q | C | G | L | R | A | P | Q¹³⁷ |
| SEQ ID NO: 16 | 127-146 | ¹²⁷K | R | E | L | R | N | L | P | Q | Q | C | G | L | R | A | P | Q | R | C | D¹⁴⁶ |
| SEQ ID NO: 17 | 136-155 | ¹³⁶Q | C | G | L | R | A | P | Q | R | C | D | L | D | V | E | S | G | G | R | D¹⁵⁵ |
| SEQ ID NO: 18 | 138-157 | ¹³⁸G | L | R | A | P | Q | R | C | D | L | D | V | E | S | G | G | R | D | R | Y¹⁵⁷ |

FIGURE 1

(Part 1)

(Part 2)

(Part 3)

SEQUENCE LISTING

```
<160> NUMBER OF SEQ ID NOS: 18

<210> SEQ ID NO 1
<211> LENGTH: 157
<212> TYPE: PRT
<213> ORGANISM: Peanut Ara h 2

<400> SEQUENCE: 1

Leu Thr Ile Leu Val Ala Leu Ala Leu Phe Leu Leu Ala Ala His Ala
1               5                   10                  15
```

-continued

```
Ser Ala Arg Gln Gln Trp Glu Leu Gln Gly Asp Arg Arg Cys Gln Ser
            20                  25                  30
Gln Leu Glu Arg Ala Asn Leu Arg Pro Cys Glu Gln His Leu Met Gln
        35                  40                  45
Lys Ile Gln Arg Asp Glu Asp Ser Tyr Glu Arg Asp Pro Tyr Ser Pro
 50                  55                  60
Ser Gln Asp Pro Tyr Ser Pro Ser Pro Tyr Asp Arg Arg Gly Ala Gly
 65                  70                  75                  80
Ser Ser Gln His Gln Glu Arg Cys Cys Asn Glu Leu Asn Glu Phe Glu
                85                  90                  95
Asn Asn Gln Arg Cys Met Cys Glu Ala Leu Gln Gln Ile Met Glu Asn
            100                 105                 110
Gln Ser Asp Arg Leu Gln Gly Arg Gln Gln Glu Gln Gln Phe Lys Arg
        115                 120                 125
Glu Leu Arg Asn Leu Pro Gln Gln Cys Gly Leu Arg Ala Pro Gln Arg
130                 135                 140
Cys Asp Leu Asp Val Glu Ser Gly Gly Arg Asp Arg Tyr
145                 150                 155

<210> SEQ ID NO 2
<211> LENGTH: 20
<212> TYPE: PRT
<213> ORGANISM: Peanut Ara h 2

<400> SEQUENCE: 2

Leu Thr Ile Leu Val Ala Leu Ala Leu Phe Leu Leu Ala Ala His Ala
 1               5                  10                  15
Ser Ala Arg Gln
            20

<210> SEQ ID NO 3
<211> LENGTH: 20
<212> TYPE: PRT
<213> ORGANISM: Peanut Ara h 2

<400> SEQUENCE: 3

Phe Leu Leu Ala Ala His Ala Ser Ala Arg Gln Gln Trp Glu Leu Gln
 1               5                  10                  15
Gly Asp Arg Arg
            20

<210> SEQ ID NO 4
<211> LENGTH: 20
<212> TYPE: PRT
<213> ORGANISM: Peanut Ara h 2

<400> SEQUENCE: 4

Arg Gln Gln Trp Glu Leu Gln Gly Asp Arg Arg Cys Gln Ser Gln Leu
 1               5                  10                  15
Glu Arg Ala Asn
            20

<210> SEQ ID NO 5
<211> LENGTH: 20
<212> TYPE: PRT
<213> ORGANISM: Peanut Ara h 2

<400> SEQUENCE: 5

Arg Arg Cys Gln Ser Gln Leu Glu Arg Ala Asn Leu Arg Pro Cys Glu
 1               5                  10                  15
```

```
<210> SEQ ID NO 6
<211> LENGTH: 20
<212> TYPE: PRT
<213> ORGANISM: Peanut Ara h 2

<400> SEQUENCE: 6

Ala Asn Leu Arg Pro Cys Glu Gln His Leu Met Gln Lys Ile Gln Arg
1               5                   10                  15

Asp Glu Asp Ser
            20

<210> SEQ ID NO 7
<211> LENGTH: 20
<212> TYPE: PRT
<213> ORGANISM: Peanut Ara h 2

<400> SEQUENCE: 7

Leu Met Gln Lys Ile Gln Arg Asp Glu Asp Ser Tyr Glu Arg Asp Pro
1               5                   10                  15

Tyr Ser Pro Ser
            20

<210> SEQ ID NO 8
<211> LENGTH: 20
<212> TYPE: PRT
<213> ORGANISM: Peanut Ara h 2

<400> SEQUENCE: 8

Asp Ser Tyr Glu Arg Asp Pro Tyr Ser Pro Ser Gln Asp Pro Tyr Ser
1               5                   10                  15

Pro Ser Pro Tyr
            20

<210> SEQ ID NO 9
<211> LENGTH: 20
<212> TYPE: PRT
<213> ORGANISM: Peanut Ara h 2

<400> SEQUENCE: 9

Pro Ser Gln Asp Pro Tyr Ser Pro Ser Pro Tyr Asp Arg Arg Gly Ala
1               5                   10                  15

Gly Ser Ser Gln
            20

<210> SEQ ID NO 10
<211> LENGTH: 20
<212> TYPE: PRT
<213> ORGANISM: Peanut Ara h 2

<400> SEQUENCE: 10

Pro Tyr Asp Arg Arg Gly Ala Gly Ser Ser Gln His Gln Glu Arg Cys
1               5                   10                  15

Cys Asn Glu Leu
            20

<210> SEQ ID NO 11
<211> LENGTH: 20
<212> TYPE: PRT
<213> ORGANISM: Peanut Ara h 2

<400> SEQUENCE: 11
```

Gln His Leu Met
        20

```
Ser Gln His Gln Glu Arg Cys Cys Asn Glu Leu Asn Glu Phe Glu Asn
1               5                   10                  15

Asn Gln Arg Cys
            20

<210> SEQ ID NO 12
<211> LENGTH: 20
<212> TYPE: PRT
<213> ORGANISM: Peanut Ara h 2

<400> SEQUENCE: 12

Glu Leu Asn Glu Phe Glu Asn Asn Gln Arg Cys Met Cys Glu Ala Leu
1               5                   10                  15

Gln Gln Ile Met
            20

<210> SEQ ID NO 13
<211> LENGTH: 20
<212> TYPE: PRT
<213> ORGANISM: Peanut Ara h 2

<400> SEQUENCE: 13

Arg Cys Met Cys Glu Ala Leu Gln Gln Ile Met Glu Asn Gln Ser Asp
1               5                   10                  15

Arg Leu Gln Gly
            20

<210> SEQ ID NO 14
<211> LENGTH: 20
<212> TYPE: PRT
<213> ORGANISM: Peanut Ara h 2

<400> SEQUENCE: 14

Ile Met Glu Asn Gln Ser Asp Arg Leu Gln Gly Arg Gln Gln Glu Gln
1               5                   10                  15

Gln Phe Lys Arg
            20

<210> SEQ ID NO 15
<211> LENGTH: 20
<212> TYPE: PRT
<213> ORGANISM: Peanut Ara h 2

<400> SEQUENCE: 15

Gln Gly Arg Gln Gln Glu Gln Gln Phe Lys Arg Glu Leu Arg Asn Leu
1               5                   10                  15

Pro Gln Gln Cys
            20

<210> SEQ ID NO 16
<211> LENGTH: 20
<212> TYPE: PRT
<213> ORGANISM: Peanut Ara h 2

<400> SEQUENCE: 16

Lys Arg Glu Leu Arg Asn Leu Pro Gln Gln Cys Gly Leu Arg Ala Pro
1               5                   10                  15

Gln Arg Cys Asp
            20

<210> SEQ ID NO 17
<211> LENGTH: 20
```

```
<212> TYPE: PRT
<213> ORGANISM: Peanut Ara h 2

<400> SEQUENCE: 17

Gln Cys Gly Leu Arg Ala Pro Gln Arg Cys Asp Leu Asp Val Glu Ser
1               5                   10                  15

Gly Gly Arg Asp
            20

<210> SEQ ID NO 18
<211> LENGTH: 20
<212> TYPE: PRT
<213> ORGANISM: Peanut Ara h 2

<400> SEQUENCE: 18

Gly Leu Arg Ala Pro Gln Arg Cys Asp Leu Asp Val Glu Ser Gly Gly
1               5                   10                  15

Arg Asp Arg Tyr
            20
```

IMMUNOINTERACTIVE MOLECULES AND USES THEREOF

FIELD OF THE INVENTION

The present invention relates generally to molecules such as peptides, polypeptides and proteins which interact immunologically with T lymphocytes in subjects having peanut allergy, or allergy to other tree nuts, and genetic sequences encoding same. These molecules are preferentially immunointeractive with T cells in subjects having an allergy to the Ara h 2 allergen. The molecules of the present invention are useful in the development of diagnostic, therapeutic and prophylactic agents for conditions characterised by an aberrant, inappropriate or otherwise unwanted immune response to Ara h 2 or derivative or homologue thereof.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Peanut allergy is a life-threatening and incurable disorder, affecting approximately 1% of the general population (Sicher et al., *J Allergy Clin Immunol* 103: 559-562, 1999). It is characterised by the sudden onset of anaphylaxis, which may occur with exposure to minute quantities of peanut proteins (Hourihane et al., *J Allergy Clin Immunol* 100: 596-600, 1997). Nut induced anaphylaxis is that most frequently associated with mortality or with life-threatening features (Sampson et al, *N Engl J Med* 327: 380-4, 1992). Peanut proteins are frequently concealed within apparently safe food sources, such that accidental contact occurs for up to 50% of sufferers over a 5 year period (Sicherer et al., *Paediatrics* 102: e6, 1998). Not surprisingly, nut allergy is associated with significant psychological morbidity for sufferers and carers alike, akin to that suffered by those with chronic debilitating illnesses such as rheumatoid arthritis (Primeau et al., *Clin Exp Allergy* 30: 1135-43, 2000). Cure, while being an imperative to remove nut allergy as a cause of mortality, is also necessary to remove the chronic psychological burden that peanut allergic subjects carry.

To date, efforts at immunotherapy for peanut allergy have been met by extremely limited success. Nelson et al. have shown that tolerance of peanut can be induced using a rush immunotherapy protocol, but that tolerance is lost in approximately half of the subjects during maintenance dosing and additionally that injections are associated with frequent episodes of anaphylaxis in the majority of subjects during both the buildup and maintenance phases (Nelson et al., *J Allergy Clin Immunol* 99: 744-51, 1997). Oppenheimer et al. demonstrated similar findings within their study, again showing that active therapy is associated with a high rate of systemic anaphylaxis. Data collection in that study was terminated after the administration of peanut extract to a placebo randomised subject resulted in their death, highlighting the dangerous nature of this condition (Oppenheimer et al., *J Allergy Clin Immunol* 90: 256-62, 1992).

Development of novel strategies to overcome the morbidity associated with allergen immunotherapy depends on an accurate understanding of the immunological basis to successful immunotherapy, as well as its side-effects. It has long been established that morbidity due to allergen immunotherapy is due to the cross-linking of IgE, and that this action is not required for such therapy to be efficacious (Litwin et al., *Int Arch Allergy Appl Immunol* 87: 361-61, 998). It is also known that one of the critical actions of immunotherapy in producing tolerance is its ability to change the predominant specific T cell phenotype from a $T_H2$ to a $T_H1$ phenotype (Robinson, *Br Med Bull* 56: 956-968, 2000). Although the precise pathway through which this change occurs remains undocumented, current theories suggest that this is likely to occur via the suppression of the $T_H2$ phenotype by IL-10, then reconstitution of a normal immune response via the actions of IL-2 and IL-15 (Akdis et al., *Allergy* 55: 522-530, 2000).

A key difference in antibody and lymphocyte responses is in antigen recognition, antibodies recognising conformational epitopes dependent on molecular tertiary structure, while CD4+ T cells recognise short linear peptides. This difference in antigen recognition is the basis to many novel strategies of immunotherapy, including that using peptides based upon T cell epitopes, B cell epitope mutants and altered peptide ligands (Akdis et al., *Trends Immunol* 22: 175-8, 2001). Such methods all depend on the alteration or absence molecular tertiary structure, so that IgE cross-linking and effector cell activation is lost. Peptide immunotherapy is the method for which the best evidence of efficacy exists, being documented for both cat dander allergy and bee venom allergy. Muller et al. (1998) showed that, in the absence of any systemic side-effects, tolerance could be achieved for the major bee venom allergen Phospholipase A2 (PLA2) using sequences based on its three major epitopes, while several authors have demonstrated that peptides based on the structure of the major cat allergen Fel d 1 can be used to induce diminished-clinical responses (Muller et al., *J Allergy Clin Immunol* 101: 747-754, 1998; Norman et al., *Am J Respir Crit Care Med* 154: 1623-8, 1996; Marcotte et al., *J Allergy Clin Immunol* 101: 506-13, 1998; Pene et al., *J Allergy Clin Immunol* 102: 571-8, 1998; Maguire et al., *Clin Immunol* 93: 222-31, 1999). Crucial to the development of such strategies is the retention of T cell epitopes, so that T cell phenotypic change can be induced.

Accordingly, there is a need to both identify the major peanut allergens and, further, to identify the T cell epitopes of these allergens. The identification characterisation, and analysis of these epitopes is critical to the development of specific diagnostic and immunotherapeutic methodology.

In work leading up to the present invention, the inventors have identified the human T cell epitopes of the peanut allergen, Ara h 2. The identification of Ara h 2 T cell epitopes now facilitates the development of molecules and methodology for the diagnosis and treatment of conditions characterised by the aberrant, inappropriate or otherwise unwanted immune response to Ara h 2 or derivative or homologue thereof such as peanut allergy or other tree-nut allergy.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains amino acid and nucleotide sequence information prepared using the programme PatentIn Version 3.1, presented herein after the bibliography. Each amino acid or nucleotide sequence is identified in the sequence listing by the numeric indicator <201> followed by the sequence identifier (eg. <210>1, <210>2, etc). The length, type of sequence (DNA, protein, etc) and source organism for each amino acid or nucleotide sequence is indicated by information provided in the numeric indicator fields <211>, <212> and <213>, respectively. Amino acid and nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention provides an isolated peptide of the formula:

$$X_1 X_2 X_3$$

wherein:
  $X_1$ and $X_3$ may be the same or different and each is an amino acid sequence comprising from 0 to 40 naturally or non-naturally occurring amino acid residues;
  $X_2$ is any amino acid sequence derived from or homologous to Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

Another aspect of the present invention provides an isolated peptide of the formula:

$$X_1 X_2 X_3$$

wherein:
  $X_1$ and $X_3$ may be the same or different and each is an amino acid sequence comprising from 0 to 40 naturally or non-naturally occurring amino acid residues;
  $X_2$ is an amino acid sequence of from 5 to 100 residues derived from, homologous to or contiguous with amino acids 1-157 inclusive or derivatives thereof of Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, mutant, chemical equivalent or mimetic of said peptide.

Yet another aspect of the present invention provides an isolated peptide of the formula:

$$X_1 X_2 X_3$$

wherein
  $X_1$ and $X_3$ may be the same or different and each is an amino acid sequence comprising from 0 to 40 naturally or non-naturally occurring amino acid residues;
  $X_2$ is an amino acid sequence of from 5 to 100 residues derived from, homologous to or contiguous with amino acids 19-92, 91-119 and/or 127-155 inclusive or derivatives thereof of Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

Still another aspect of the present invention provides a peptide, as hereinbefore defined, wherein the antibody reactivity of said peptide is inhibited, abrogated or otherwise down-regulated.

Yet another aspect of the present invention provides an isolated peptide comprising any amino acid sequence derived from or homologues to Ara h 2 wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

A further aspect of the present invention provides an isolated peptide comprising an amino acid sequence of from 5-100 residues derived from, homologues to or contiguous with amino acids 1-157 inclusive or derivatives thereof of Ara h 2 wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

In yet another aspect, the present invention provides a nucleic acid molecule comprising a sequence of nucleotides encoding or complementary to a sequence encoding the peptides as hereinbefore defined or a derivative, homologue or analogue thereof.

In still another aspect the present invention provides a method for the treatment and/or prophylaxis of a condition in a subject, which condition is characterised by the aberrant, unwanted or otherwise inappropriate immune response to Ara h 2, said method comprising administering to said subject an effective amount of a peptide as hereinbefore defined for a time and under conditions sufficient to remove or reduce the presence or function in said subject of T cells directed to said Ara h 2.

A further aspect of the present invention contemplates the use of an agent as hereinbefore defined in the manufacture of a medicament for the treatment of a condition in a mammal, which condition is characterised by an aberrant, unwanted or otherwise inappropriate immune response to Ara h 2.

In yet another further aspect, the present invention contemplates a pharmaceutical composition comprising an agent as hereinbefore defined and one or more pharmaceutically acceptable carriers and/or diluents. Said agents are referred to as the active ingredients.

Yet another aspect of the present invention relates to agents, as hereinbefore defined, when used in the method of the present invention.

Still another aspect of the present invention is directed to a method of diagnosing or monitoring a condition in a mammal, which condition is characterised by an aberrant, unwanted or inappropriate response to Ara h 2, said method comprising screening for Ara h 2 reactive T cells utilising the peptides hereinbefore defined.

In another aspect the present invention provides diagnostic kits for use in the diagnostic methodology hereinbefore defined.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 1 is a schematic representation of Ara h 2 20-mer peptide series. Peptides of 20 amino acids in length, overlapping by 11 amino acids except for those at the N-terminus (18 amino acid overlap), representing the entire amino acid sequence of Ara h 2 were used. The residue numbers of each peptide is shown in the left hand column, while overlap with peptides located adjacent to each peptide is demonstrated by the extent to which each peptide is overlaid within the figure. Peptide sequences are based upon the Ara h 2 sequence described by Stanley et al (Stanley et al, *Arch Biochem Biophys*. 342: 244-253, 1997) (SEQ ID NO: 1).

a. Mitogenicity Assay

Triplicate cultures of $5 \times 10^4$ cells/well of a 3 week oligoclonal HDM-specific TCL together with $5 \times 10^4$ cells/well of irradiated autologous PBMC and Ara h 2 peptides at a concentration of 10 µg/ml for 72 hours. For the last 12 hours cells were pulsed with $^3$H-thymidine before harvesting and counting. $^3$H-thymidine incorporation for each peptide was estimated and expressed as mean cpm+SEM.

b. Toxicity Assay

Triplicate cultures of $5 \times 10^4$ cells/well of a 3 week oligoclonal HDM-specific TCL stimulated with 50 IU/ml of recombinant human IL-2 and Ara h 2 peptides at a concentration of 10 µg/ml for 72 hours. For the last 12 hours cells were pulsed with 0.1 mCu/well $^3$H-thymidine before harvesting and counting. $^3$H-thymidine incorporation for each peptide was estimated and expressed as mean cpm+SEM.

Figure 3:
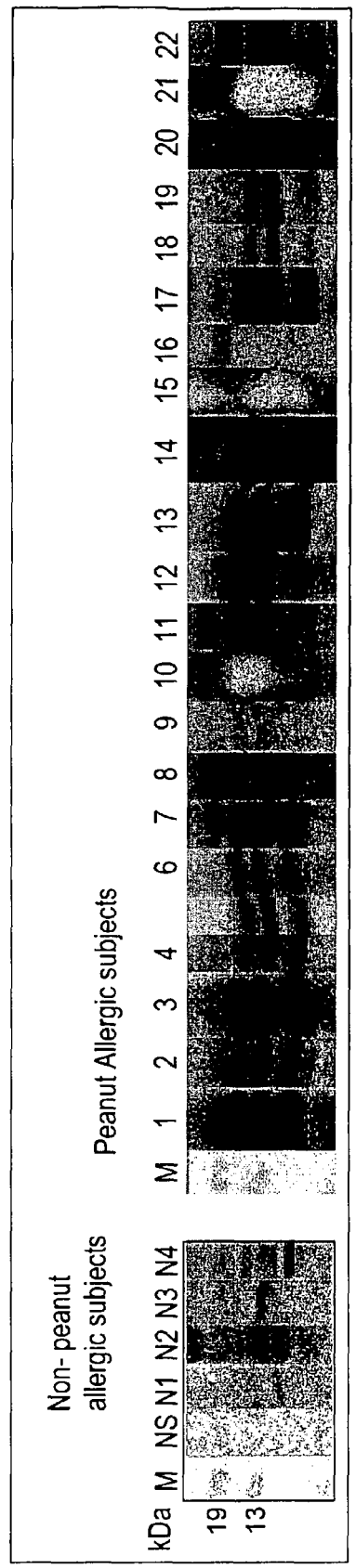

FIG. 3 is an image of a Western blot for serum IgE reactivity to Ara h 2 of peanut allergic and non-allergic subjects.

Legend: M, molecular mass; NS, no serum.

Following resolution of CPE on a 14% polyacrylamide gel, proteins were transferred to nitrocellulose and probed with sera from the study population, and non-peanut allergic controls. IgE was detected using HRP conjugated mouse anti-human IgE and enhanced chemiluminescence.

Figure 4:
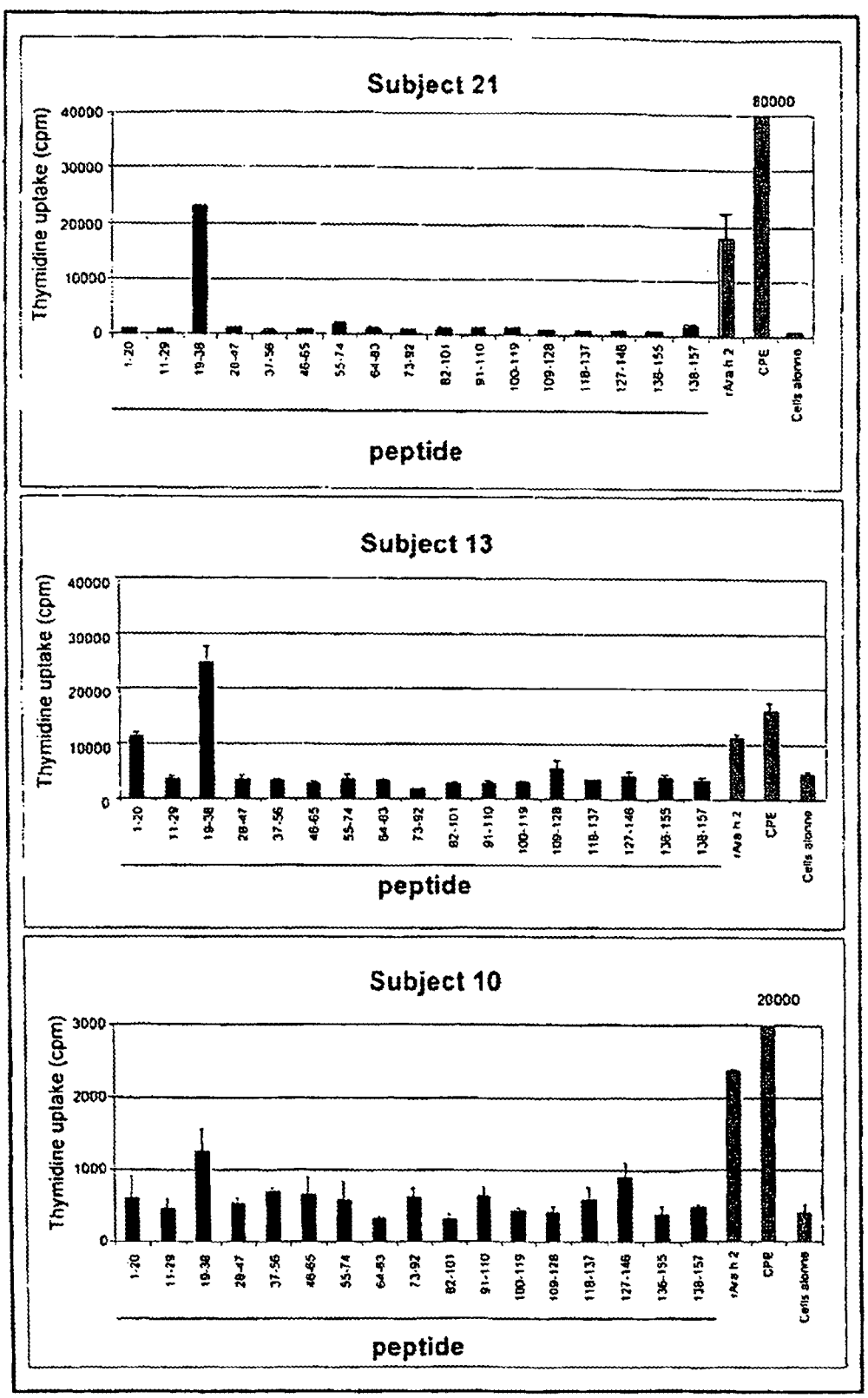
Figure 4:
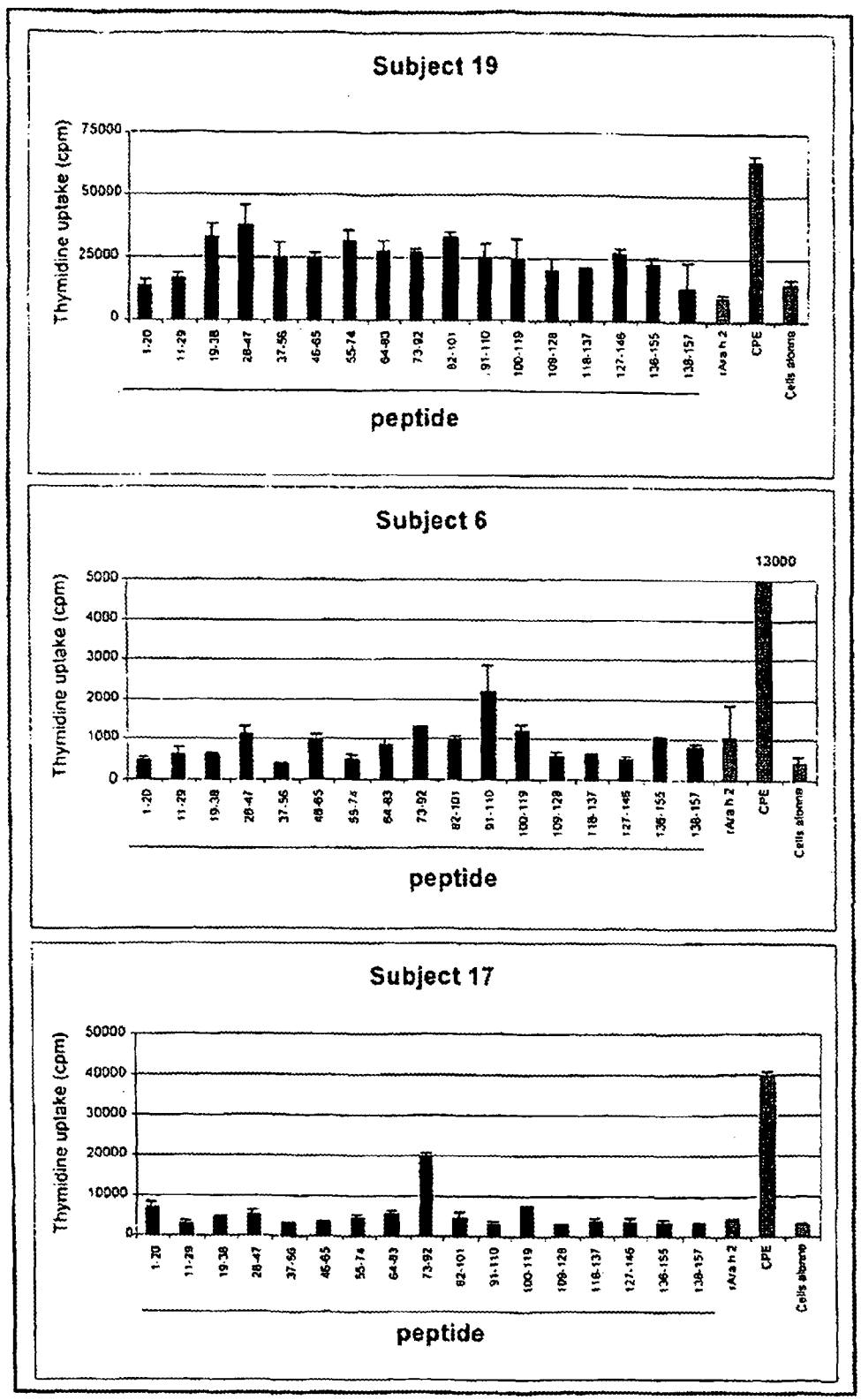
Figure 4:
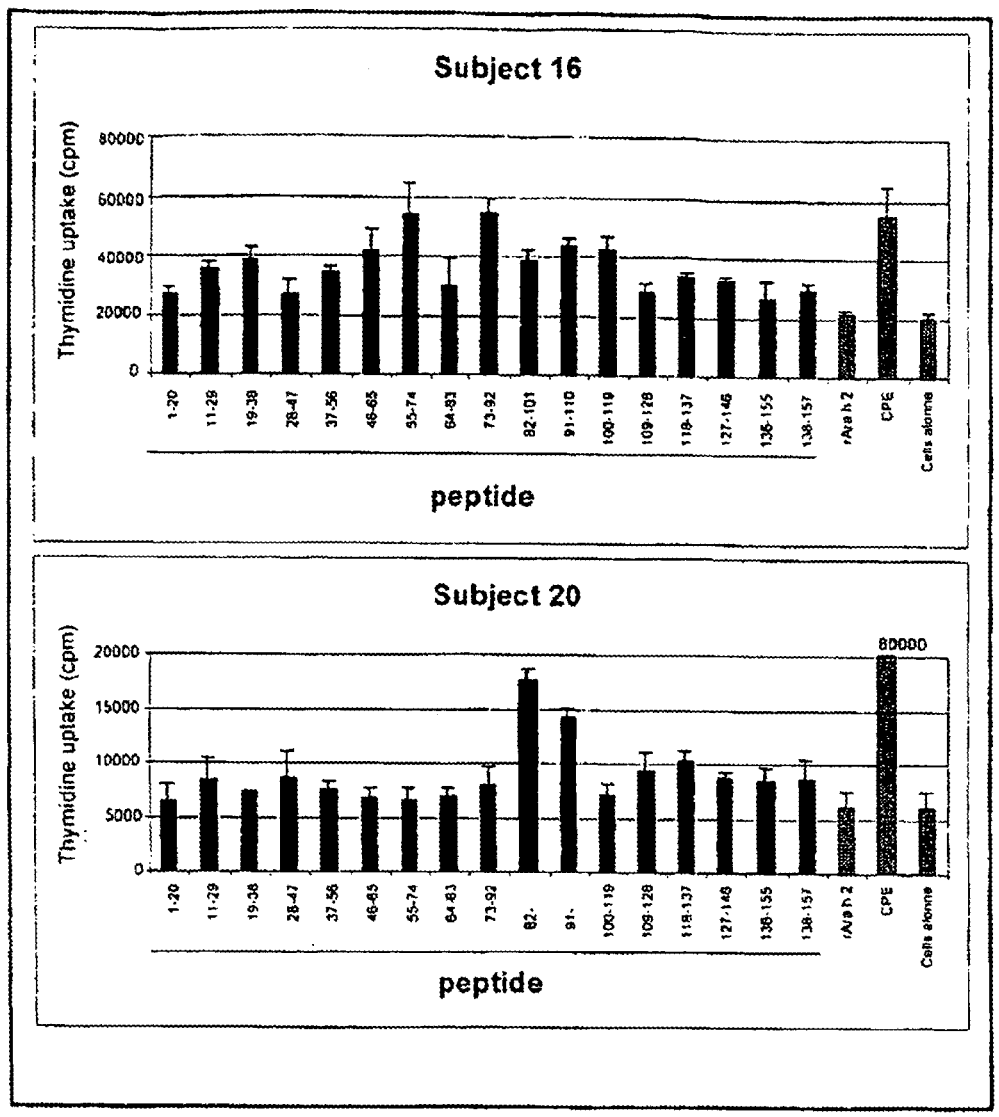

FIG. 4 is a graphical representation of peanut allergic donor peanut specific TCL proliferative responses to Ara h 2 peptides, Ara h 2 and crude peanut extract. Peanut specific TCL ($5 \times 10^4$ cells/ml) from individuals with peanut allergy generated using CPE were stimulated with Ara h 2 peptides at a concentration of 10 µg/ml in the presence of autologous irradiated PBMC as APC ($5 \times 10^4$ cells/ml) in 3 day cultures. Proliferative responses were assessed by tritiated thymidine incorporation, and displayed as mean cpm+SEM of triplicate cultures.

Figure 5:
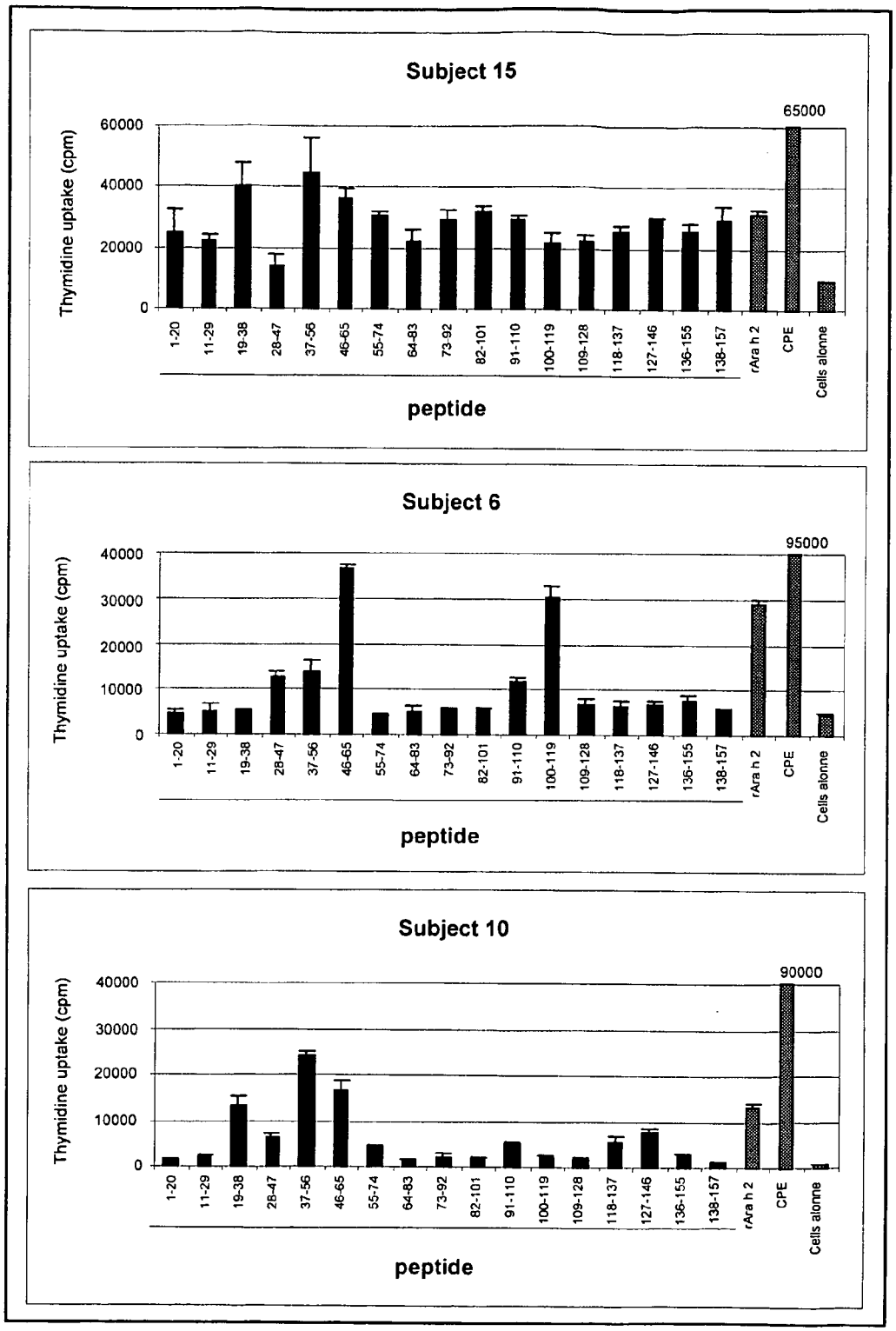

FIG. 5 is a graphical representation of peanut allergic donor peanut specific Ara h 2 pulsed TCL proliferative responses Ara h 2 peptides, Ara h 2 and crude peanut extract. Peanut specific TCL ($5 \times 10^4$ cells/ml) from individuals with peanut allergy were generated using CPE and rAra h 2, then stimulated with Ara h 2 peptides at a concentration of 10 pg/ml in the presence of autologous irradiated PBMC as APC ($5 \times 10^4$ cells/ml) in 3 day cultures. Proliferative responses were assessed by tritiated thymidine incorporation, and displayed as mean cpm+SEM of triplicate cultures.

Figure 6:
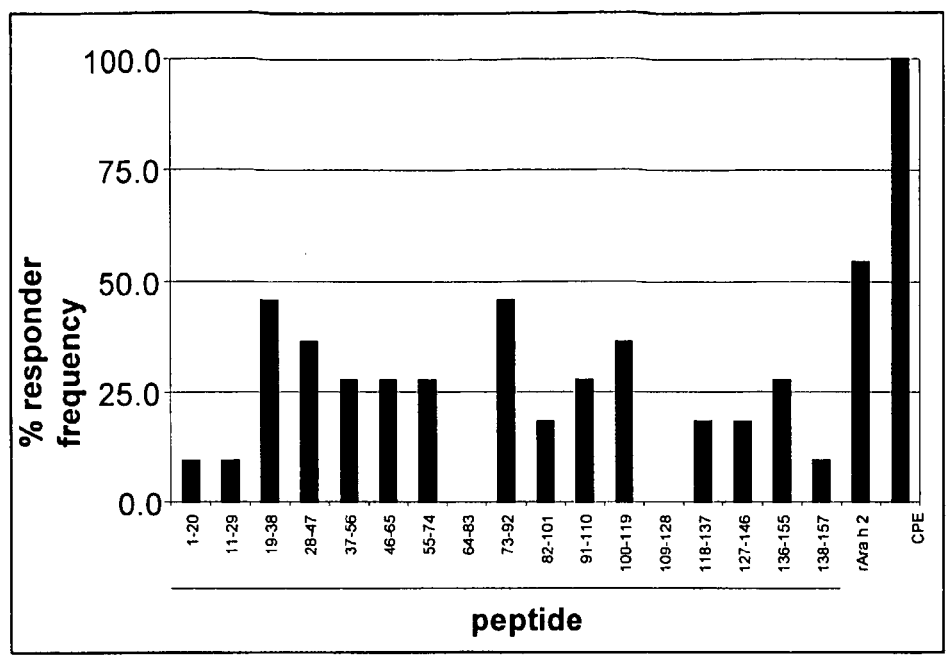

FIG. 6 is a graphical representation of the percentage responder frequency to Ara h 2 peptides amongst peptide responsive CPE driven TCL. The percentage of peptide responsive TCLs demonstrating a stimulation index of $\geq 2.5$ to individual peptides is demonstrated, along with responses to rAra h 2 and CPE.

Figure 7:
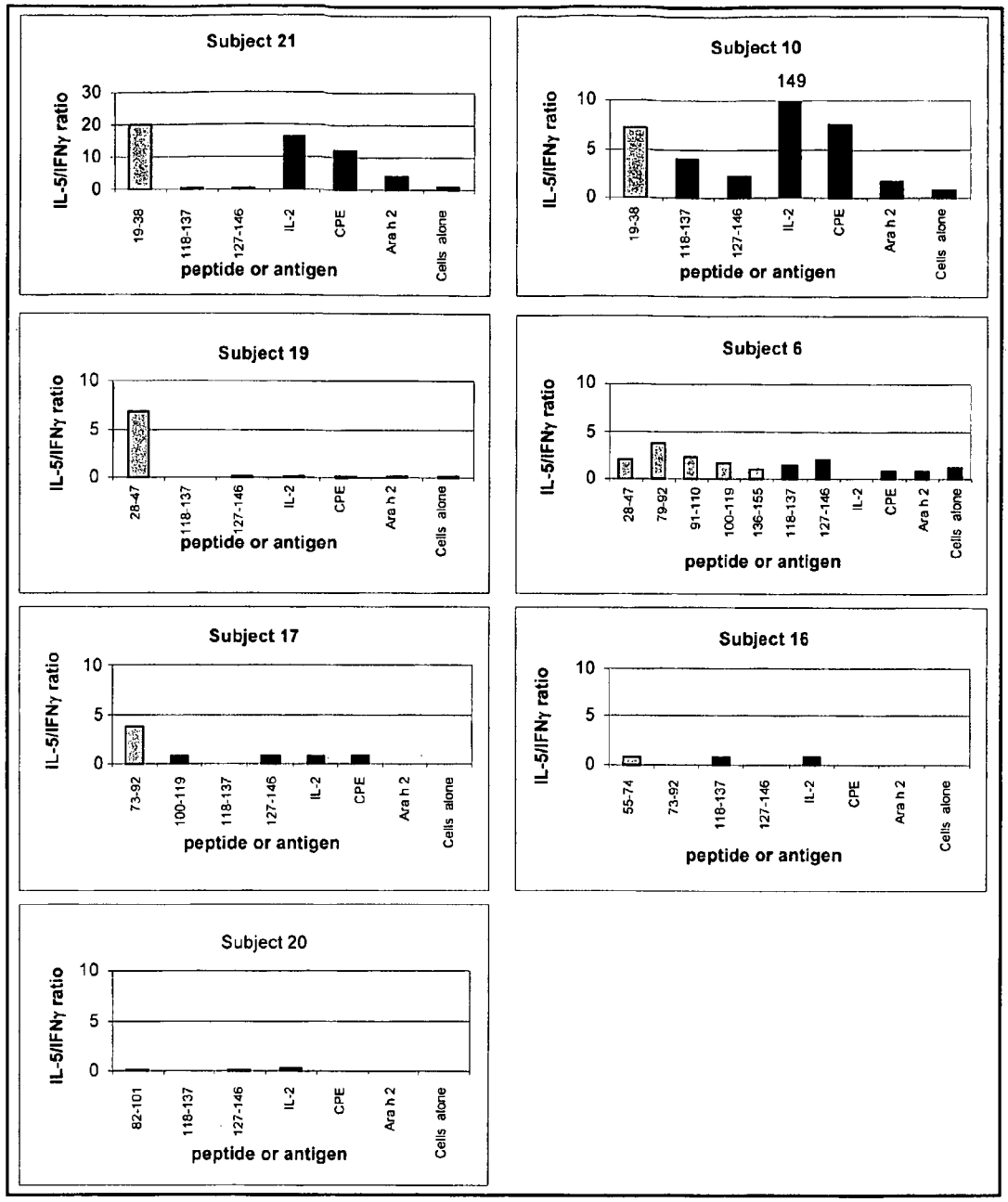

FIG. 7 is a graphical representation of peanut allergic donor peanut specific Ara h 2 pulsed TCL cytokine responses to Ara h 2 peptides, Ara h 2 and crude peanut extract. Peanut specific TCLs ($5 \times 10^4$/ml) from individuals with peanut allergy were generated using CPE, then stimulated with Ara h 2 peptides at a concentration of 10 ug/ml in the presence of autologous irradiated PBMC as APC ($5 \times 10^4$/ml) in 3 day cultures. Cytokine supernatants were collected after 48 hours culture and assayed by specific ELISA. Data is displayed graphically as IL-5:IFN-γ ratio. Peptides associated with a significant proliferative response are shaded grey.

Figure 8:
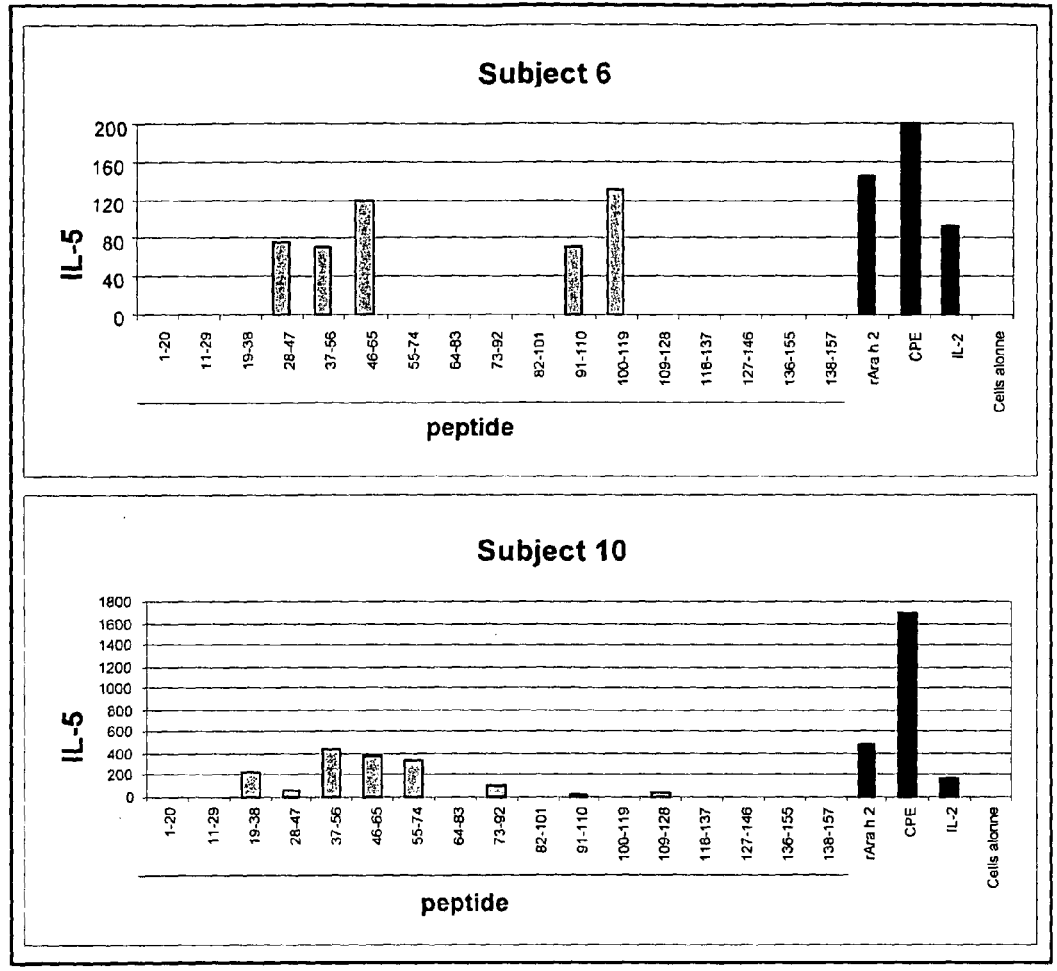

FIG. 8 is a graphical representation of peanut allergic donor Ara h 2 pulsed TCL cytokine responses to Ara h 2 peptides, Ara h 2 and crude peanut extract. Peanut specific TCL ($5 \times 10^4$ cells/ml) from individuals with peanut allergy generated using CPE and pulsed with rAra h 2, were stimulated with Ara h 2 peptides at a concentration of 10 µg/ml in the presence of autologous irradiated PBMC as APC ($5 \times 10^4$ cells/ml) in 3 day cultures. Cytokine supernatants were collected after 48 hours culture and assayed by specific ELISA. Data are displayed graphically as IL-5 concentration (pg/ml). Peptides associated with a significant proliferative response are shaded grey.

DETAILED DESCRIPTION OF THE INVENTION

The present invention is predicated, in part, on the identification of Ara h 2 T cell epitopic regions. The identification of immunodominant epitopes of Ara h 2 has enabled the improvement of diagnostic methodology and the development of therapeutic and prophylactic compositions and treatment approaches for conditions such as, but not limited to, peanut allergy. In accordance with the present invention, overlapping peptides were synthesised based on the Ara h 2 amino acid sequence disclosed in SEQ ID NO:1. The T cell immunoreactivity of these peptides is identified in accordance with the present invention on the basis of the interactivity of T cell lines generated from the peripheral blood of subjects with peanut allergies. The identification and generation of those molecules thereby forms the basis for a new range of diagnostic, therapeutic and prophylactic reagents and procedures.

Accordingly, one aspect of the present invention provides an isolated peptide of the formula:

$$X_1X_2X_3$$

wherein:
$X_1$ and $X_3$ may be the same or different and each is an amino acid sequence comprising from 0 to 40 naturally or non-naturally occurring amino acid residues;
$X_2$ is any amino acid sequence derived from or homologous to Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

Without limiting the present invention in any way, peanuts contain many proteins, with the number of distinct bands visible on SDS-PAGE depending on the methodology used. Up to 53 bands are visible following high pressure liquid chromatography (de Jong et al., *Clin Exp Allergy* 28: 743-51, 1998). Only two of these proteins warrant classification as major allergens using standard criteria, whereby IgE reactivity occurs within greater than 50% of the peanut allergic population; these proteins are termed Ara h 1 and Ara h 2 (Burks et al., *Allergy* 53: 725-30, 1998).

Ara h 2 is a glycoprotein which has been identified as a member of the conglutin seed storage family. 20% of the Ara h 2 molecular mass represents carbohydrate side chains and it migrates as a doublet on SDS-PAGE with an average molecular mass of 17.5 kDa (Burks et al, *Int Arch Allergy Immunol* 119:165-172, 1992). It has been characterised as a major allergen, on the basis of its reactivity with 6 out of 6 sera tested (Burks et al, 1992, supra). Others have also confirmed its importance Clarke demonstrated that 71% of subjects possessed specific IgE to Ara h 2 upon western blotting of crude peanut extract. Kleber-Janke et al. have demonstrated that 85% of subjects possessed IgE towards their recombinant form upon western blotting, and de Jong's group have shown that approximately 78% of their group demonstrate specific IgE to purified natural Ara h 2 (Clarke et al., *Clin Exp Allergy* 28: 1251-7, 1998; de Jong et al, 1998 supra; Kleber-Janke et al., *Int Arch Allergy Immunol* 119: 265-274, 1999). Linear epitope mapping has demonstrated 10 IgE binding epitopes throughout Ara h 2, with 3 potentially immunodominant.

Reference to "Ara h 2" should be understood to include reference to all forms and components of Ara h 2 or derivatives, mutants, homologues, analogues, equivalents or mimetics thereof. Reference to "Ara h 2" should also be understood to include reference to all protein forms of Ara h 2 or its functional equivalent or derivative including, for example, any isoforms which may arise from alternative splicing of Ara h 2 mRNA. It includes reference to mutants, polymorphic variants or homologues of Ara h 2. It also includes reference to analogues or equivalents of Ara h 2 such as may occur where a product which naturally comprises Ara h 2 is synthetically generated for the purpose of generating a product such as a food additive. The present invention thereby provides epitopes and methods for their use in the diagnosis and treatment of any condition characterised by hypersensitivity to an Ara h 2 or Ara h 2-like molecule such as peanut allergy or a tree-nut allergy. Preferably, said Ara h 2 comprises the sequence set forth in SEQ ID NO:1 or is a derivative, homologue, analogue, chemical equivalent, mutant or mimetic of said sequence.

The present invention therefore more particularly provides an isolated peptide of the formula:

$$X_1X_2X_3$$

wherein:
$X_1$ and $X_3$ may be the same or different and each is an amino acid sequence comprising from 0 to 40 naturally or non-naturally occurring amino acid residues;
$X_2$ is an amino acid sequence of from 5 to 100 residues derived from, homologous to or contiguous with amino acids 1-157 inclusive or derivatives thereof of Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, mutant, chemical equivalent or mimetic of said peptide.

Still more particularly the present invention provides an isolated peptide of the formula:

$$X_1X_2X_3$$

wherein
$X_1$ and $X_3$ may be the same or different and each is an amino acid sequence comprising from 0 to 40 naturally or non-naturally occurring amino acid residues;
$X_2$ is an amino acid sequence of from 5 to 100 residues derived from, homologous to or contiguous with amino acids 19-92, 91-137 and/or 127-155 inclusive or derivatives thereof of Ara h 2;
and wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

Still more particularly, $X_2$ is any amino acid sequence of from 5 to 100 residues derived from, homologous to or contiguous with amino acids 19-38, 28-47, 37-56, 46-65, 55-74, 73-92, 82-101, 91-110, 100-119, 118-137, 127-146 and/or 136-155 inclusive or derivatives thereof of Ara h 2.

Yet more particularly, $X_2$ is any amino acid sequence of from 5 to 100 residues derived from homologous to or contiguous with amino acids 19-38, 28-47, 73-92, 91-110 and/or 100-119 inclusive or derivatives thereof of Ara h 2.

Most particularly, $X_2$ is any amino acid sequence of from 5 to 100 residues derived from, homologous to or contiguous with amino acids 19-38, 28-47, 73-92 and/or 100-119 inclusive or derivatives thereof of Ara h 2.

Reference to "T cells" should be understood as a reference to any cell comprising a T cell receptor. In this regard, the T cell receptor may comprise any one or more of the α, β, γ or δ chains. The present invention is not intended to be limited to any particular functional sub-class of T cells although in a preferred embodiment the subject T cell is a T helper cell and still more preferably a Th2-type cell. In this regard, reference to "modifying T cell function" should be understood as a reference to modifying any one or more functions which a T cell is capable of performing. For example, the subject function may be proliferation, differentiation or other form of cellular functional activity such as the production of cytokines. Preferably, the subject functional activity is proliferation.

In terms of modifying the function of T cells from subjects having a condition characterised by an aberrant, unwanted or inappropriate immune response to Ara h 2, it should be understood that this is not necessarily a reference to modifying the function of all the T cells in a given sample but is likely, in fact, to reflect the modification or functioning of only some of the T cells in the sample. For example, only a portion of the T helper cells in a given T cell sample may functionally respond to contact with the subject peptide. Such a partial response should be understood to fall within the scope of the present invention. It should also be understood that the T cells which are derived from the subject may be freshly harvested T cells or they may have undergone some form of in vitro or in vivo manipulation prior to testing. For example, T cell lines may have been generated from the cell sample and it is these T cell lines which then form the subject derived T cell population which is tested in accordance with the present invention. To the extent that the subject functional activity is T cell proliferation, the T cell proliferation assay is preferably performed as disclosed herein. Still more preferably, the subject modification of T cell function is the induction of a proliferation index of $\geq 2.5$.

Reference to an "aberrant, unwanted or otherwise inappropriate" immune response should be understood as a reference to any form of physiological activity which involves the activation and/or functioning of one or more immune cells where that activity is inappropriate in that it is of an inappropriate type or proceeds to an inappropriate degree. It may be aberrant in that according to known immunological principals it either should not occur when it does so or else should occur when it does not do so. In another example, the immune response may be inappropriate in that it is a physiologically normal response but which is unnecessary and/or unwanted, such as occurs with respect to type-I hypersensitivity responses to innocuous allergens. Preferably said immune response is peanut hypersensitivity.

By "peanut hypersensitivity" it should be understood to mean the exhibition of clinical symptoms of IgE mediated peanut hypersensitivity. However, it should be understood that although clinical symptoms may be evident, not all such individuals would necessarily exhibit detectable levels of peanut specific serum IgE which is measured using the Kallestad Allercoat EAST System (Sanofi-Pasteur Diagnostics, USA), although such individuals should nevertheless be understood to fall within the scope of the definition of those exhibiting "peanut hypersensitivity". Alternatively, testing may proceed utilising either the Pharmacia or the UniCap systems.

In a preferred embodiment, $X_2$ comprises not less than about 5 and not greater than about 50 amino acid residues, more preferably not less than about 5 and not greater than about 30 amino acid residues and even more preferably not less than about 5 and not greater than about 20. Most preferably, $X_2$ comprises 5, 6, 7, 8, 9, 10, 11, 12, 13, 14, 15, 16, 17, 18, 19 or 20 amino acids.

In a particularly preferred embodiment, $X_2$ comprises a sequence of at least 5 amino acids derived from one or more of the following amino acid sequences:

| | |
|---|---|
| RQQWELQGDRRCQSQLERAN | (SEQ ID NO:4) |
| RRCQSQLERANLRPCEQHLM | (SEQ ID NO:5) |
| PYDRRGAGSSQHQERCCNEL | (SEQ ID NO:10) |
| RCMCEALQQIMENQSDRLQG | (SEQ ID NO:13) |

More preferably, $X_2$ comprises a sequence of at least 5 amino acids derived from one or more of SEQ ID NO:4 or SEQ ID NO:5.

Reference to a "peptide" includes reference to a peptide, polypeptide or protein or parts thereof. The peptide may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "peptide" includes a peptide comprising a sequence of amino acids as well as a peptide associated with other molecules such as amino acids, lipids, carbohydrates or other peptides, polypeptides or proteins.

"Derivatives" include fragments, parts, portions and variants from natural, synthetic or recombinant sources including fusion proteins. Parts or fragments include, for example, active regions of the subject peptide. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Chemical and functional equivalents of the subject peptide should be understood as molecules exhibiting any one or more of the functional activities of these molecules and may be derived from any source such as being chemically synthesized or identified via screening processes such as natural product screening.

Homologues include peptides derived from varieties other than peanuts, such as peptides derived from other tree nuts.

The derivatives include fragments having particular epitopes or parts of the entire protein fused to peptides, polypeptides or other proteinaceous or non-proteinaceous molecules.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues. Mutants include molecules which exhibit modified functional activity (for example, Ara h 2 peptides which express one or more T cell epitopes but lack B cell reactivity).

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | a-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |

TABLE 2-continued

| Non-conventional amino acid | Code | Non-conventional amino acid | Code |
|---|---|---|---|
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

It is possible to modify the structure of a peptide according to the invention for various purposes such as for increasing solubility, enhancing therapeutic or preventative efficacy, enhancing stability or increasing resistance to proteolytic degradation. A modified peptide may be produced in which the amino acid sequence has been altered, such as by amino acid substitution, deletion or addition, to modify immunogenicity and/or reduce allergenicity. Similarly components may be added to peptides of the invention to produce the same result.

For example, a peptide can be modified so that it exhibits the ability to induce T cell anergy. In this instance, critical binding residues for the T cell receptor can be determined using known techniques (for example substitution of each residue and determination of the presence or absence of T cell reactivity) In one example, those residues shown to be essential to interact with the T cell receptor can be modified by replacing the essential amino acid with another, preferably similar amino acid residue (a conservative substitution) whose presence is shown to alter T cell reactivity or T cell functioning. In addition, those amino acid residues which are not essential for T cell receptor interaction can be modified by being replaced by another amino acid whose incorporation may then alter T cell reactivity or T cell functioning but does not, for example, eliminate binding to relevant MHC proteins. In yet another example, mutant peptides may be created which exhibit normal T cell binding but abrogated IgE binding.

Exemplary conservative substitutions are detailed in Table 3, below, and include:

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Such modifications will result in the production of molecules falling within the scope of "mutants" of the subject peptide as herein defined. "Mutants" should be understood as a reference to peptides which exhibit one or more structural features or functional activities which are distinct from those exhibited by the non-mutated peptide counterpart. Peptides of the invention may also be modified to incorporate one or more polymorphisms resulting from natural alielic variation and D-amino acids, non-natural amino acids or amino acid analogues may be substituted into the peptides to produce modified peptides which fall within the scope of the invention.

Peptides may also be modified by conjugation with polyethylene glycol (PEG) by known techniques. Reporter groups may also be added to facilitate purification and potentially increase solubility of the peptides according to the invention. Other well known types of modification including insertion of specific endoprotease cleavage sites, addition of functional groups or replacement of hydrophobic residues with less hydrophobic residues as well as site-directed mutagenesis of DNA encoding the peptides of the invention may also be used to introduce modifications which could be useful for a wide range of purposes. The various modifications to peptides according to the invention which have been mentioned above are mentioned by way of example only and are merely intended to be indicative of the broad range of modifications which can be effected.

In related aspects, the method of the present invention provides a mutant form of the peptides hereinbefore defined wherein said peptide molecule retains all or some of its capacity to interact with T cells but exhibits partially or completely inhibited, abrogated or otherwise down-regulated antibody reactivity. Effecting the down-regulation of antibody reactivity can be achieved by any suitable method, which methods would be well known to those skilled in the art. For example, to the extent that a B cell epitope is defined by its linear amino acid sequence, one may add, delete or substitute one or more amino acid residues in order to render the mutated linear sequence distinct from the naturally occurring sequence. To the extent that an epitope may be additionally, or alternatively, defined by a conformational epitope, one may seek to disrupt that conformation by disrupting a 2° or, to the extent that homodimers or heterodimers exist, a 3° structure of the peptide. This may be achieved, for example, by disrupting the formation of bonds, such as disulphide bonds, which are known to stabilise 2° and/or 3° structures.

Accordingly, in a related aspect the present invention provides a peptide, as hereinbefore defined, wherein the antibody reactivity of said peptide is inhibited, abrogated or otherwise down-regulated.

More preferably, said antibody is IgE.

Another aspect of the present invention provides an isolated peptide comprising any amino acid sequence derived from or homologues to Ara h 2 wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

More particularly, the present invention provides an isolated peptide comprising an amino acid sequence of from 5-100 residues derived from, homologues to or contiguous with amino acids 1-157 inclusive or derivatives thereof of Ara h 2 wherein said peptide molecule is capable of interacting with T cells and modifying T cell function when incubated with cells from subjects having a condition characterised by an aberrant, unwanted or otherwise inappropriate immune response to Ara h 2 or a derivative, homologue, analogue, mutant, chemical equivalent or mimetic of said peptide.

In one preferred embodiment said amino acid sequence is derived from, homologous to or contiguous with amino acids 1-92, 91-137 and/or 127-155 inclusive or derivatives thereof of Ara h 2.

In another preferred embodiment said amino acid sequence is derived from, homologous to or contiguous with amino acids 19-38, 28-47, 37-56, 46-65, 55-74, 73-92, 82-101, 91-110, 100-119, 118-137, 127-146 and/or 136-155 inclusive or derivatives thereof of Ara h 2.

In yet another preferred embodiment said amino acid sequence is derived from, homologous to or contiguous with amino acids 19-38, 28-47, 73-92, 91-110 and/or 100-119 inclusive or derivatives thereof of Ara h 2.

More preferably, said amino acid sequence is derived from, homologous to or contiguous with amino acids 1-38, 28-47, 73-92 and/or 100-119 inclusive or derivatives thereof of Ara h 2.

In another aspect said amino acid sequence comprises a sequence of at least 5 amino acids derived from one or more of the following amino acid sequences:

| | |
|---|---|
| RQQWELQGDRRCQSQLERAN | (SEQ ID NO:4) |
| RRCQSQLERANLRPCEQHLM | (SEQ ID NO:5) |
| PYDRRGAGSSQHQERCCNEL | (SEQ ID NO:10) |
| RCMCEALQQIMENQSDRLQG | (SEQ ID NO:13) |

According to this aspect, said amino acid sequence preferably comprises a sequence of at least 5 amino acids derived from one or more of SEQ ID NO:4 or SEQ ID NO:5.

The peptides of the present invention may be prepared by recombinant or chemical synthetic means. According to a preferred aspect of the present invention, there is provided a recombinant peptide or mutant thereof which is preferentially immunologically reactive with T cells from individuals with peanut hypersensitivity, which is expressed by the expression of a host cell transformed with a vector coding for the peptide sequence of the present invention. The peptide may be fused to another peptide, polypeptide or protein. Alternatively, the peptide may be prepared by chemical synthetic techniques, such as by the Merrifield solid phase synthesis procedure. Furthermore, although synthetic peptides of the formula given above represent a preferred embodiment, the present invention also extends to biologically pure preparations of the naturally occurring peptides or fragments thereof. By "biologically pure" is meant a preparation comprising at least about 60%, preferably at least about 70%, or preferably at least about 80% and still more preferably at least about 90% or greater as determined by weight, activity or other suitable means.

The present invention should therefore be understood to encompass peptides that comprise at least one T or B cell epitope of Ara h 2 in conjunction with other amino acids (which may or may not be naturally occurring as amino acid analogues) or other chemical species. In a preferred aspect of the invention such peptides may comprise one or more epitopes of Ara h 2, which epitopes may be T or B cell epitopes. Peptides with one or more epitopes of Ara h 2 are desirable for increased therapeutic effectiveness.

In another aspect, the present invention provides a nucleic acid molecule comprising a sequence of nucleotides encoding or complementary to a sequence encoding the peptides as hereinbefore defined or a derivative, homologue or analogue thereof.

It should be understood that reference to "peptides" includes reference to peptides comprising one or more T cell epitopes. A nucleic acid molecule encoding the subject peptide is preferably a sequence of deoxyribonucleic acids such as cDNA or a genomic sequence. A genomic sequence may comprise exons and introns. A genomic sequence may also include a promoter region or other regulatory regions.

The nucleic acid molecule may be ligated to an expression vector capable of expression in a prokaryotic cell (eg. *E. coli*) or a eukaryotic cell (eg. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptide which forms are encompassed by the present invention.

Such nucleic acids may be useful for recombinant production of T cell epitopes of Ara h 2 or proteins comprising them by insertion into an appropriate vector and transfection into a suitable cell line. Such expression vectors and host cell lines also form an aspect of the invention.

In producing peptides by recombinant techniques, host cells transformed with a nucleic acid having a sequence encoding a peptide according to the invention or a functional equivalent of the nucleic acid sequence are cultured in a medium suitable for the particular cells concerned. Peptides can then be purified from cell culture medium, the host cells or both using techniques well known in the art such as ion exchange chromatography, gel filtration chromatography, ultrafiltration, electrophoresis or immunopurification with antibodies specific for the peptide.

Nucleic acids encoding Ara h 2 or peptides comprising T and/or B cell epitopes of Ara h 2 may be expressed in bacterial cells such as *E. coli*, insect cells, yeast or mammalian cells such as Chinese hamster ovary cells (CHO). Suitable expression vectors, promoters, enhancers and other expression control elements are referred to in Sambruck et al (1989). Other suitable expression vectors, promoters, enhancers and other expression elements are well known to those skilled in the art. Examples of suitable expression vectors in yeast include Yep Sec 1 (Balderi et al., 1987, *Embo J.*, 6.229-234); pMFa (Kurjan and Herskowitz., 1982, *Cell.*, 30:933-943); JRY88 (Schultz et al., 1987, *Gene.*, 54.113-123) and pYES2 (Invitrogen Corporation, San Diego, Calif.). These vectors are freely available as are baculovirus and mammalian expression systems. For example, a baculovirus system is commercially available (ParMingen, San Diego, Calif.) for expression in insect cells while the pMsg vector is commercially available (Pharmacia, Piscataway, N.J.) for expression in mammalian cells.

For expression in *E. coli* suitable expression vectors include among others, pTrc (Amann et al., 1998, Gene., 69:301-315) pGex (Amrad Corporation, Melbourne, Australia); pMal (N.E. Biolabs, Beverley, Mass.); pRit5 (Pharmacia, Piscataway, N.J.); pEt-11d (Novagen, Maddison, Wis.) (Jameel et al., 1990, *J. Virol.*, 64.3963-3966) and pSem (Knapp et al., 1990, *Bio Techniques.*, 8.280-281). The use of pTRC, and pEt-11d, for example, will lead to the expression of unfused protein. The use of pMal, pRit5, pSem and pGex will lead to the expression of allergen fused to maltose E binding protein (pMal), protein A (pRit5), truncated-galactosidase (PSEM) or glutathione S-transferase (pGex). When a T cell epitope of Ara h 2 or a peptide comprising it is expressed as a fusion protein, it is particularly advantageous to introduce an enzymatic cleavage site at the fusion junction between the carrier protein and the peptide concerned. The peptide of the invention may then be recovered from the fusion protein through enzymatic cleavage at the enzymatic site and biochemical purification using conventional techniques for purification of proteins and peptides. The different vectors also have different promoter regions allowing constitutive or inducible expression or temperature induction. It may additionally be appropriate to express recombinant peptides in different *E. coli* hosts that have an altered capacity to degrade recombinantly expressed proteins. Alternatively, it may be advantageous to alter the nucleic acid sequence to use codons preferentially utilised by *E. coli*, where such nucleic acid alteration would not effect the amino acid sequence of the expressed proteins.

Host cells can be transformed to express the nucleic acids of the invention using conventional techniques such as calcium phosphate or calcium chloride co-precipitation, DEAE-dextran-mediated transfection or electroporation. Suitable methods for transforming the host cells may be found in Sambruck et al. (1989), and other laboratory texts. The nucleic acid sequence of the invention may also be chemically synthesised using standard techniques.

In addition to recombinant production of peptides according to the invention, the nucleic acids may be utilised as probes for experimental or purification purposes.

The identification of T cell epitopic regions facilitates the identification and/or rational design of a range of mutant peptide molecules. As detailed hereinbefore, these mutant peptides may comprise one or more mutated T cell epitopes and/or B cell epitopes. In this regard, there is provided scope for the generation of mutant peptides comprising mutated B cell epitopes or combinations of intact versus mutated B and T cell epitopes. The applications of these molecules are described in more detail below but in a preferred embodiment relate to modulation of the peanut hypersensitivity immune response in terms of either a prophylactic or therapeutic treatment.

Identification and synthesis of the Ara h 2 T cell epitopes as disclosed herein now facilitates the development of a range of diagnostic and prophylactic/therapeutic treatment protocols for use with respect to peanut related immune conditions. Also facilitated is the development of reagents for use therein. Accordingly, the present invention should be understood to extend to the use of the peptides or functional derivatives, homologues, analogues or mutants thereof in the therapeutic and/or prophylactic treatment of patients. Such methods of treatment include, but are not limited to:

(i) Administration of the subject peptides or mutants thereof to a patient as a means of desensitising or inducing immunological tolerance to Ara h 2 or Ara h 2-like molecules. This may be achieved, for example, by inducing Ara h 2 directed Th2 anergy or apoptosis. Such an outcome may be achieved by any one of a number of techniques including the use of peptides which maintain T cell epitope reactivity but which either naturally or as a result of mutation are unable to undergo IgE binding. Alternatively, one may utilise desensitisation/treatment protocols which are based on the administration of specific concentrations of a given peptide in accordance with a specific regime in order to induce tolerance. Such methodology may eliminate Ara h 2 hypersensitivity or it may reduce the severity of Ara h 2 hypersensitivity.

Preferably such treatment regimes are capable of modifying the T cell response or both the B and T cell response of the individual concerned. As used herein, modification of the allergic response of the individual suffering from peanut hypersensitivity can be defined as inducing either non-responsiveness or diminution in symptoms to the Ara h 2 molecule as determined by standard clinical procedures (Varney et al. 1991 *British Medical Journal* 302:265-269). Diminution in the symptoms includes any reduction in an allergic response in an individual to Ara h 2 after a treatment regime has been completed.

This diminution may be subjective or clinically determined, for example by using standard skin tests known in the art.

Exposure of an individual to the peptides of the present invention, which peptides comprise at least one T cell epitope, may tolerise or anergise appropriate T cell subpopulations such that they become unresponsive to Ara h 2 and do not participate in stimulating an immune response upon such exposure. Preferably the peptides according to the invention will retain immunodominant T cell epitopes but possess abrogated IgE binding.

Administration of a peptide of the invention may modify the cytokine secretion profile as compared with exposure to naturally occurring Ara h 2 allergen. This exposure may also influence T cell subpopulations which normally participate in the allergic response to migrate away from the site or sites of normal exposure to the allergen and towards the site or sites of therapeutic administration. This redistribution of T cell subpopulations may ameliorate or reduce the ability of an individual's immune system to stimulate the usual immune response at the site of normal exposure to the allergen, resulting in diminution of the allergic symptoms.

Modification of the B cell response may be achieved, for example, via modulation of the cytokine profile produced by T cells, as detailed above. Specifically, decreasing T cell derived IL-4 and IL-13 production thereby decreasing IgE synthesis.

(ii) The peptides of the present invention may be used in the capacity of an adsorbent to remove Ara h 2 directed T cells from a biological sample or from a patient.

Accordingly, in another aspect the present invention provides a method for the treatment and/or prophylaxis of a condition in a subject, which condition is characterised by the aberrant, unwanted or otherwise inappropriate immune response to Ara h 2, said method comprising administering to said subject an effective amount of a peptide as hereinbefore defined for a time and under conditions sufficient to remove or reduce the presence or function in said subject of T cells directed to said Ara h 2.

Preferably said condition is hypersensitivity to peanuts or tree nuts which contain Ara h 2 or Ara h 2-like molecules, such as hazelnuts, almonds or Brazil nuts.

An "effective amount" means an amount necessary at least partly to attain the desired immune response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

The subject of the treatment or prophylaxis is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Administration of the peptide of the present invention (herein referred to as "agent") in the form of a pharmaceutical composition, may be performed by any convenient means. The agent of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of an agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The agent may be administered in a convenient manner such as by the oral, intravenous (where water soluble), intraperitoneal, intramuscular, subcutaneous, intradermal, intranasal, sublingual or suppository routes or implanting (e.g. using slow release molecules). The agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

Another aspect of the present invention contemplates the use of an agent as hereinbefore defined in the manufacture of a medicament for the treatment of a condition in a mammal, which condition is characterised by an aberrant, unwanted or otherwise inappropriate immune response to Ara h 2.

Preferably said condition is hypersensitivity to peanuts or a tree nut which contains Ara h 2 or Ara h 2-like molecules, such as a hazelnut.

In yet another further aspect, the present invention contemplates a pharmaceutical composition comprising an agent as hereinbefore defined and one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding a modulatory agent. The vector may, for example, be a viral vector.

Routes of administration include, but are not limited to, respiratorily (eg. intranasally or orally via aerosol), intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant. Preferably, said route of administration is subcutaneously, intradermally or intranasally.

Yet another aspect of the present invention relates to agents, as hereinbefore defined, when used in the method of the present invention.

In yet another aspect, the present invention should be understood to extend to the use of the peptides of the present invention in diagnostic applications. Said diagnostic applications include, but are not limited to:

(i) To measure the reactivity of a subject's cells to Ara h 2. This is of use, for example, with respect to the diagnosis and/or monitoring of conditions characterised by an aberrant, unwanted or otherwise inappropriate immune response to Ara h 2. The peptides may be added into solution or bound to a solid support together with cells derived from peripheral blood or from tissue biopsies either unfractionated, fractionated or derived as a continuous cell line. Reactivity to the subject peptide may then be measured by standard proliferation assays such as incorporation of $H^3$-thymidine, measurement of expressed or secreted molecules such as surface markers, cytokines or other standard assays of cellular activity which are well known in the art.

(ii) The use of T cell epitope comprising peptides together with a T cell proliferation assay which utilises a T cell sample derived from the subject will facilitate, for example, the identification of a T cell responsive population.

Methods of detecting Ara h 2 may be utilised, for example, to qualitatively or quantitatively detect Ara h 2 levels. However, these methods may also be utilised to screen for mutations or polymorphisms in Ara h 2 which mutations may result in, for example, loss of T cell reactivity to Ara h 2. These methods may be utilised for the purpose of screening for peptide molecules suitable for use in therapeutically or prophylactically treating an individual suffering from Ara h 2 related hypersensitivity.

Accordingly, yet another aspect of the present invention is directed to a method of diagnosing or monitoring a condition in a mammal, which condition is characterised by an aberrant, unwanted or inappropriate response to Ara h 2, said method comprising screening for Ara h 2 reactive T cells utilising the peptides hereinbefore defined.

Preferably said condition is hypersensitivity to peanuts or tree nuts which contain Ara h 2 or Ara h 2-like molecules, such as hazelnuts, almonds or Brazil nuts.

In another embodiment the present invention provides diagnostic kits for use in the diagnostic methodology hereinbefore defined.

The present invention will now be further described with reference to the following non-limiting Examples.

Example 1

Materials & Methods

The materials and methods detailed in this example were utilised in relation to the Example 2 data.

1. Materials
Tissue Culture Reagents
Ara h 2 20-mer peptides Chiron Mimotopes, Australia
Ficoll-Paque (research grade) Amersham Biosciences, Sweden
Foetal Bovine Serum (FBS) Gibco BRL, USA
Human AB+ serum Sigma Chemical Company, USA
Penicillin-Streptomycin-Glutamine Gibco BRL, USA
Phytohaemagglutinin (PHA) Wellcome Diagnostics, England
Recombinant human IL-2 (rIL-2) Cetus Corporation, USA
RPMI 1640 (glutamine free) Gibco BRL, USA
Sodium heparin (preservative free) David Bull Laboratories, Australia
Tetanus toxoid Laboratory stocks
Cell Lines and Bacterial Transfectants
rAra h 2 transfected BL-21 E. coli Kind gift of Ms M de Leon
Immunoblotting Reagents
Nitrocellulose membrane (BA 0.45 µm) Schleicher and Schuell, Germany
Rabbit anti-mouse/human immunoglobulin—Dako Corporation, Denmark
horseradish peroxidase (HRPO) conjugate
Skim milk powder Diploma, Australia
Ponceau S Sigma Chemical Company, USA
Enhanced chemiluminescence reagent Pierce, USA
ELISA Reagents
Biotinylated rat-anti-human IFN-γ Endogen, USA
Biotinylated rat-anti-human IL-5 PharMingen, USA
Human recombinant IFN-γ Endogen, USA
Human recombinant IL-5 PharMingen, USA
Mouse anti-human IFN-γ Endogen, USA
Mouse anti-human IL-5 PharMingen, USA
Streptavidin-biotinylated HRPO complex Amersham, USA
Enhanced chemiluminescence reagent Perkin Elmer, USA
Flow Cytometry Reagents
Mouse anti-human CD4-FITC PharMingen, USA
Mouse anti-human CD4-FITC/CD8-PE Becton Dickinson, USA
Mouse anti-human CD3-FITC/CD19-PE Becton Dickinson, USA
Mouse anti-human CD45-FITC/CD14-PE Becton Dickinson, USA
Mouse $IgG_1$-FITC/$IgG_1$-PE isotype control Becton Dickinson, USA
Mouse $IgG_1$-APC isotype control PharMingen, USA
Mouse $IgG_1$-FITC isotype control PharMingen, USA
Mouse $IgG_1$-PE isotype control PharMingen, USA
Phorbol 12-myristate 13-acetate (PMA) Sigma Chemical Company, USA
General Reagents
Dialysis tubing (MW cut off 3.5 kDa) Pierce, USA General Chemicals
Ammonium persulphate (AP) Bio-Rad Laboratories, USA
Ampicillin Sigma Chemical Company, USA
Aqueous counting scintillant (ASCII) Ajax Chemicals, Australia
Bis-acrylamide, electrophoresis purity Bio-Rad Laboratories, USA
Bovine Serum Albumin (BSA) Sigma Chemical Company, USA
Bovine γ-globulin (BGG) Sigma Chemical Company, USA
Bromophenol blue BDH Laboratory Supplies, UK
Coomassie Brilliant Blue R-250 Bio-Rad Laboratories, USA
Dimethylpimelimidate (DMP) Sigma Chemical Company, USA
Dimethylsulphoxide (DMSO) Sigma Chemical Company, USA
Dithiothreitol (DTT) Sigma Chemical Company, USA
Ethanol, 95% (absolute) Ajax Chemicals, Australia
Glacial acetic acid Ajax Chemicals, Australia
Glycerol Ajax Chemicals, Australia
Glycine Ajax Chemicals, Australia
Hydrogen chloride Ajax Chemicals, Australia
Hydrogen peroxide ($H_2O_2$) (30%) Ajax Chemicals, Australia
Hydrogen sulphate ($H_2SO_4$), analytical grade Ajax Chemicals, Australia
Isopropyl-β-D-thiogalactoside (IPTG) Sigma Chemical Company, USA
Methanol Ajax Chemicals, Australia
Polyethylene glycol (average MW 20,000) BDH Laboratory Supplies, UK
Ponceau S Sigma Chemical Company, USA
Protein assay dye reagent Pierce Laboratories, USA prestained markers
Sodium azide ($NaN_3$) BDH Laboratory Supplies, UK
Sodium carbonate ($Na_2CO_3$) Ajax Chemicals, Australia
Sodium chloride (NaCl) Ajax Chemicals, Australia
Sodium dihydrogen orthophosphate Sigma Chemical Company, USA ($NaH_2PO_4.2H_2O$)
Sodium dodecyl sulphate (SDS) Bio-Rad Laboratories, USA
Sodium hydrogen carbonate ($NaHCO_3$) BDH Laboratory Supplies, UK
Sodium phosphate ($Na_2HPO_4$) Sigma Chemical Company, USA
N,N,N',N'-Tetramethylethylene-diamine (TEMED) Bio-Rad Laboratories, USA
$^3$H-thymidine (methyl) DuPont, USA
Trichloroacetic acid (TCA) BDH Laboratory Supplies, UK
Triethanolamine BDH Laboratory Supplies, UK
Tris (hydroxymethyl) aminomethane (Tris) BDH Laboratory Supplies, UK
Trypan blue Calbiochem, USA
Tryptone Becton Dickinson, USA
Tween 20 (Polyxyethylenesorbitan monolaurate) Sigma Chemical Company, USA
Yeast extract Sigma Chemical Company, USA 2. Buffers and Solutions All buffers and solutions were prepared in Milli Q (Millipore, USA) $H_2O$ unless otherwise stated.

Acrylamide-Bis (50% w/v)

A commercially available premixed preweighed acrylamide/bis powder was diluted in 162 ml water (Bio-Rad Laboratories, USA) to yield a 50% solution. This was stored at room temperature, protected from light.

Ammonium Persulphate (10% w/v)

A 10% ammonium persulphate solution was prepared by adding 1 g ammonium persulphate to 10 ml $H_2O$. This solution was stored at 4° C. for up to 3-4 days.

Binding Buffer

A 0.1 M $Na_2HPO_4$ solution, adjusted to pH 9.0, was prepared and stored at room temperature.

10% Milk Powder 10 g of skim milk powder dissolved in 100 ml PBS.

BGG Standard for the Pierce Protein Assay 1.45 mg BGG was dissolved in 1 ml $H_2O$, stored at $-20°$ C. in 100 µl aliquots and used for the standard curve in the Pierce protein assay (Pierce, USA) according to the manufacturer's instructions.

Coomassie Brilliant Blue R-250

A 0.2% (w/v) Coomassie Brilliant Blue R-250 (Coomassie Blue) solution was prepared by dissolving 0.2 g of Coomassie Brilliant Blue R-250 in 100 ml of 50% (v/v) methanol, 10% (v/v) glacial acetic acid in $H_2O$. This solution was filtered through Whatman #1 filter paper and stored at room temperature in the dark.

Destaining Solution

Coomassie Blue stained gels were destained using 7% glacial acetic acid. The destaining solution was prepared by diluting 70 ml glacial acetic acid to 1 L with $H_2O$.

ELISA Coating Buffer, pH 9.6

This buffer consisted of 0.86 g $Na_2CO_3$ and 1.72 g $NaHCO_3$ dissolved in 100 ml $H_2O$ and was stored at 4° C. The pH of this solution was as indicated and did not need to be adjusted.

Elution Buffer

A 500 ml solution containing 500 mM imidazole, 50 mM $NaH_2PO4$, 300 mM NaCl, and 8 M urea was prepared and stored at room temperature.

FACS Wash Buffer (1% FBS/0.02% NaN3/PBS)

5 ml of FBS and 1.54 ml of 1 M $NaN_3$ solution was added to 443.46 ml of PBS and the solution stored at 4° C.

FBS-15% DMSO

To 50 ml of FBS, 8.8 ml of DMSO was added to yield a 15% DMSO solution. This was aliquoted into 10 ml polypropylene tubes and stored at $-20°$ C. until required.

Luria-Agar (L-Agar)

To 1 L of L-broth 15 g of agar was added and the solution sterilised by autoclaving.

Luria-Broth (L-Broth)

L-broth was prepared by the addition of 5 g of tryptone, 2.5 g of yeast extract and 2.5 g of NaCl to 450 ml of water. The pH was then adjusted to 7.0 and the solution made up to 500 ml. The medium was then sterilised by autoclaving.

Lysis Buffer

A 500 ml solution containing 100 mM $NaH_2PO4$, 10 mM Tris-HCl, 8 M urea, adjusted to a pH of 8.0 using HCl was prepared and stored at room temperature.

Phosphate Buffered Saline (PBS), pH 7.2

A 10× stock solution was prepared by dissolving 85 g NaCl, 3.9 g $NaH_2PO_4.2H_2O$ and 10.7 g $Na_2HPO_4$ in 1 L $H_2O$. This was stored at room temperature and diluted ten-fold when required.

PBS/0.1% BSA 0.1 g of BSA was dissolved in 100 ml of PBS, and used on the day of preparation.

PBS/Tween 20 (0.05% v/v)

PBS/Tween 20 (0.05% v/v) was prepared by adding 2.5 ml Tween 20 to 5 L PBS. This solution was stored at room temperature.

Phytohaemagglutinin (PHA) (400 µg/ml)

2 mg of lyophilised PHA was reconstituted with 5 ml $H_2O$ under sterile conditions to give a final concentration of 400 µg/ml. This was then aliquoted into 50 µl lots and stored at $-20°$ C.

Resolving Gel Buffer, pH 8.8

This buffer was prepared by adding 182 g Tris, 4.0 g SDS and $H_2O$ to 950 ml. The pH was adjusted to 8.8 with HCl and made up to 100 ml with $H_2O$. This buffer was stored at 4° C.

RPMI 1640/Penicillin-Streptamycin-Glutamine (Wash Medium)

5 ml of Penicllin-Streptamycin-Glutamine (Gibco, USA) was added to 500 ml of RPMI 1640 medium to yield final concentrations of 2 mM L-glutamine and 100 U/ml of penicillin/streptamycin. The medium was stored at 4° C. protected from light.

RPMI 1640/10 U/ml Sodium Heparin (Heparinised Medium)

5000 units of sterile preservative free sodium heparin and 5 ml of Penicillin-Streptamycin-Glutamine (Gibco, USA) was added to 500 ml of RPMI 1640 medium to yield final concentrations of 10 U/ml sodium heparin, 2 mM L-glutamine and 100 U/ml of penicillin/streptamycin. The medium was stored at 4° C. protected from light.

RPMI 1640/5% Human AB+ Serum (Complete Medium)

To 500 ml of RPMI 1640 medium, heat inactivated human AB+ serum and Penicillin-Streptamycin-Glutamine (Gibco, USA) were added to yield final concentrations of 5% human serum, 2 mM L-glutamine and 100 U/ml of penicillin and streptamycin. The medium was stored at 4° C. protected from light.

SDS Running Buffer

This buffer was prepared by dissolving 6.06 g Tris, 28.8 g glycine and 2 g SDS in 2 L $H_2O$. This solution was stored at room temperature.

SDS Reducing Sample Buffer

A stock solution was prepared by the addition of 3.8 g Tris, 11.5 g SDS, 50 ml glycerol and 100 mM (1.56 g) DDT to 500 ml $H_2O$. 0.1% bromophenol blue was added to allow tracking of the protein dye front. The buffer was stored at $-20°$ C. and thawed just prior to use.

1 M Sodium Azide 6.5 g of $NaN_3$ was carefully added to 100 ml of $H_2O$ in a fume hood and the resulting solution stored at room temperature.

Stacking Gel Buffer, pH 6.8

This buffer was prepared by the addition of 30 g Tris and 2.0 g SDS to 450 ml $H_2O$. Following adjustment of the pH with HCl the volume was made up to 500 ml with $H_2O$ and the buffer stored at 4° C.

Transfer Buffer

This buffer was prepared by adding 5.81 g Tris, 2.93 g glycine, 0.375 g SDS to 800 ml $H_2O$. This solution was stored at room temperature in the dark.

Trypan Blue (0.25% w/v)

This stain was prepared by dissolving 0.25 g trypan blue in 100 ml $H_2O$. This was filtered through Whatman #I filter paper and stored at room temperature.

Wash Buffer

A 500 ml solution containing 50 mM imidazole, 50 mM $NaH_2PO4$, 300 mM NaCl, and 8 M urea was prepared and stored at room temperature.

3. Study Population (a) Study Population

Peanut and tree nut allergic individuals were recruited from the Alfred Hospital Allergy Clinic and the Department of Pathology and Immunology, Monash University. Donors were chosen on the basis of a history of clinical symptoms of nut allergy, positive peanut or tree nut specific IgE (CAP-Pharmacia, score>1) or skin prick test (wheal>5 mm). The study was approved by the Alfred Hospital Ethics Committee and informed consent was obtained from all donors before blood was obtained.

(b) Protein Concentration Determination

To determine the protein concentration of nut and seed extracts a Pierce micro protein assay, based upon bicinchoninic acid induced detection of protein induced reduction of cuprous ion, was used (Smith et al. 1985). A 1450 µg/ml stock of BGG was used to establish a standard curve in the range of 725-6 µg/ml. Samples for testing and BGG standard were diluted in MilliQ water and plated in triplicate (25 µl/well) in a 96 well flat bottom plate (Linbro, USA). 200 µl of Pierce Micro-Protein Assay dye concentrate was added to each well and mixed well. Plates were then read in a Bio-Rad 3550 microplate reader (Bio-Rad Laboratories, USA) at 595 nm and sample concentrations extrapolated from the standard curve using Microplate manager software.

(c) Endotoxin Estimation

Endotoxin estimation was performed using a Biowhittaker Pyrogent Multi-test kit (Cambrex, USA) as per the manufacturer's instructions.

(d) Antigens

Preparation of Crude Peanut Extract, Ara h 1 and Ara h 2

Preparation of crude peanut extract, purification of natural Ara h 1 and Ara h 2 fractions, and expression of recombinant Ara h 2 is described in example 1.

Ara h 2 Peptides

All Ara h 2 peptides were synthesized based on the published amino acid sequence deduced from the cDNA sequence of Ara h 2 (Stanley et al. 1997). The Ara h 2 20-mer peptides (11-18 amino acid overlap) were purchased from Mimotopes, Clayton, Australia. Lyophilised peptides were reconstituted in sterile PBS to a concentration of 1 mg/ml and filter sterilised by passage through a 0.2 µm sterile filter. Hydrophobic peptides which would not reconstitute properly were first dissolved in a small volume (10 µl/mg peptide) of DMSO and then brought to the appropriate volume with sterile PBS and sterilised as above.

(e) SDS-Polyacrylamide Gel Electrophoresis (SDS-PAGE) and Gel Staining

Preparation of 14% SDS-polyacrylamide Mini Gels

A 14% resolving gel solution was prepared by mixing 7 ml 50% acrylamide/BIS, 9.4 ml resolving bel buffer, 250 µl 10% SDS, 7.7 ml water, 6.25 µl TEMED and 625 µl ammonium persulphate. The gel solution was transferred into a minigel casting unit (Novex, USA) up to a point approximately 2 cm from the top of the gel plates. $H_2O$ was then overlaid onto the gel solution to produce a flat gel surface and exclude atmospheric oxygen which interferes with polymerisation. Upon gel polymerisation (approximately 60 minutes), the gel surface was rinsed with $H_2O$ and a 4% stacking gel added. A solution sufficient for 4 minigels comprised 4.2 ml stacking gel buffer, 1.0 ml 50% acrylamide, 4.2 ml stacking gel buffer, 125 µl of 10% SDS, 6.3 ml $H_2O$, 5.0 µl TEMED and 1 ml ammonium persulphate. A plastic template was then inserted into the stacking gel and the gel was allowed to stand for 30 minutes to polymerise. If not used immediately, gels were stored at 4° C. in a moistened sealed plastic bag for up to 14 days.

SDS-PAGE

Gels were loaded on an electrophoresis unit (Novex, USA) and running buffer was added to the inner and outer chambers of the tank. Samples were prepared by diluting to a maximum concentration of 1.5 mg/ml in SDS-sample buffer and water and boiled for 5 minutes to ensure protein reduction, before loading onto gels. Generally 20 µl (for 10 well gels) and 10 µl (for 15 well gels) of sample was loaded per well. Where SDS-PAGE was being carried out for nitrocellulose transfer of Ara h 1, the Ara h 1 solution was diluted 1 in 10, to avoid non-specific binding of serum IgE. Low molecular weight standards (Invitrogen, USA) for gels to be stained with Coomassie Brilliant Blue were inserted at a volume of 5 Ill/well and 8 µl/ml for nitrocellulose transfer. Gels were electrophoresed at a constant current of 125 volts per gel until the dye front reached the bottom of the gel.

Coomassie Brilliant Blue Staining of SDS-PAGE Gels

Gels were stained in 0.2% Coomassie Brilliant Blue for 1 hour at room temperature and destained in destaining solution at room temperature.

(f) Immunoblotting

SDS-PAGE gels were assembled into stacks in transfer buffer as follows: blotting paper, nitrocellulose membrane, gel and blotting paper. Sample proteins and pre-stained molecular weight markers were electrophoretically transferred from SDS-PAGE gels to nitrocellulose at 30 volts for 3 hours in an Xcell II blot module (Novex, USA). Following transfer, the nitrocellulose membrane was stained with Ponceau S to ensure adequate protein transfer, then cut into strips and blocked by incubation with 10% milk powder-PBS for 1 hour at room temperature. The blocked nitrocellulose membrane was then washed in PBS and incubated with sample sera diluted 1 in 5 with 1% milk powder-PBS-Tween for all proteins except for Ara h 1, whereupon a 1 in 10 serum dilution was used. Incubation took place overnight, following which the blot was washed 3 times in PBS-Tween, 5 minutes/wash. A rabbit anti-human IgE HRPO conjugate (Dako, Denmark) diluted 1 in 500 dilution in 1% milk powder-PBS-Tween was then applied and incubated 1-2 hours at room temperature. Following washing 3 times in PBS-Tween, then 3 times in PBS for 5 minutes/wash, the membrane was incubated for 1 minute with freshly prepared chemiluminescence substrate (Du Pont, USA). Excess reagent was drained and the blot placed between two sheets of plastic transparency film. The nitrocellulose was then photographed and analysed using Labworks image acquisition software (UVP Laboratory Products, UK).

(g) Inhibition Immunoblotting

To explore IgE cross-reactivity, inhibition immunoblotting was carried out. Sera for immunoblotting were diluted 1 in 5 with 1% milk powder PBS-0.05% Tween and incubated with a range of concentrations of antigen (25-100 µg/ml sera) for two hours. To exclude false reduction in IgE binding in subsequent immunoblotting experiments via protease induced destruction, protease inhibitor tablets were added to the diluent (Roche, Germany). Immunoblotting was then carried out as described above.

(h) Cell Culture

Cryopreservation and Thawing of PBMCs and TCLs

PBMC and TCL were cryopreserved in FBS/15% DMSO in polypropylene cryovials (Greiner, Germany). Following pelleting by centrifugation, 329×g, 10 minutes, cells were resuspended in ice cold FBS/15% DMSO at a concentration of $0.5-1\times10^7$ cells/ml. Vials were placed into a "Mr Frosty" freezing container (Nalgene, USA), and placed in a −80° C. freezer overnight before transfer to liquid nitrogen (−180° C.) for long term storage. Thawing took place via placement of the frozen cell suspension within a 37° C. water bath. When thawed, the suspension was transferred to a 25 ml tube and wash medium was added drop-wise with continual mixing until 15 ml had been added. Cells were recovered by centrifugation at 329×g for 10 minutes followed by resuspension in complete medium.

Mononuclear Cell Separation from Peripheral Blood

Peripheral blood (80-100 ml) was collected by venipuncture in 50 ml syringes flushed with preservative free sodium heparin to prevent clotting. Blood was then diluted 1:1 with warm (37° C.) heparinised medium. 25 ml of diluted blood was gently layered onto 15 ml of Ficoll-Paque in a 50 ml polypropylene tube. Samples were centrifuged at 725×g for 25 minutes at room temperature, brake off. The PBMC layer (buffy coat) was harvested using a sterile disposable plastic pipette, placed into a fresh 50 ml tube and washed with RPMI/heparin medium (30 ml RPMI:20 ml PBMC). Cells were pelleted at 500×g for 15 minutes and washed in 20 ml of plain RPMI-1640, 329×g for 10 minutes. PBMC were then resuspended in RPMI/5% human AB$^+$ serum (complete medium) and the viable cell number determined by trypan blue exclusion using a haemocytometer. These cells were then used for culture immediately of cryopreserved as described above.

PBMC Proliferation Assays

1×10$^6$ PBMC/well were cultured in 96-well U bottom plates (Linbro ICN Biomedicals, USA) in 200 µl complete medium along with antigen, medium alone, tetanus toxoid and PHA (2 µg/ml) as negative and two positive controls respectively for 7 days at 37° C. in a humidified incubator, 5% $CO_2$. Cultures were pulsed for the last 16 hours with $^3$H-thymidine (1 µCi/well) and harvested onto printed glass fibre filters (Wallac, U.K.) using a 96 well automatic cell harvester (Skatron, UK). $^3$H-thymidine incorporation was measured by liquid scintillation spectroscopy with a Wallac 1205 β-counter.

Generation of Short Term T Cell Lines

Freshly harvested or frozen stored PBMC were cultured in 24-well plates (Greiner Biotechnik, Germany) at 2.5×10$^6$ cells per well (2 ml volume) in complete medium with antigen at an optimised concentration for 7 days at 37° C. in a 5% $CO_2$ humidified incubator. In the case of frozen PBMC the cells were first washed once in wash medium, 1 in 10 dilution of PBMC to medium, and pelleted at 329×g for 10 minutes to remove DMSO. At day 7 cells were washed once and resuspended at 1 to 1.5×10$^6$/ml and added together with 1×10$^6$/ml washed irradiated (3000 rads; Gammacell 1000 Elite, Nordion International, Inc.) autologous PBMC (from liquid nitrogen stocks) and antigen into fresh 24-well plates. At day 2 following restimulation, 25 U/ml of recombinant human interleukin-2 (rIL-2) was added and at day 4, 1 ml of culture medium was removed and replaced with fresh medium and 25 U/ml rIL-2. For some experiments due to low cell numbers at 2 weeks, 3 week TCLs were generated by restimulation with antigen and rIL-2 as above for a further week. In all experiments T cells were rested for 6 to 7 days after the last addition of antigen and APC.

Short Term T Cell Line Proliferation Assays 5.0×10$^4$/well TCL cells were cultured in triplicate in 96-well U bottom plates (Linbro ICN Biomedicals, USA) with antigen or medium alone and rIL-2 as negative and positive controls respectively, in the presence of autologous irradiated (3000 rads) PBMC (5.0×10$^4$/well). Cultures were incubated for 3 days. In the last 16 hours of culture, wells were pulsed with $^3$H-thymidine (1 µCi/well), then harvested onto printed glass fibre filters with a 96-well automatic cell harvester. $^3$H-thymidine incorporation was measured by liquid scintillation spectroscopy.

Assessment of Tissue Culture Reagent Mitogenicity and Toxicity

Mitogenic and toxic potential of tissue culture antigens as well as human sera used for preparation of complete medium was assessed using short term house dust mite specific TCL generated in a manner analogous to nut specific TCL. Mitogenicity was assessed via 3 days stimulation of this TCL with increasing concentrations of the relevant reagent, in the presence of autologous irradiated PBMC as APC, along with control wells containing either cells alone or house dust mite and IL-2 as negative and two positive controls respectively. For the last 16 hours of culture, cells were pulsed with $^3$H-thymidine (1 µCi/well) and harvested onto printed glass fibre filters with a 96-well automatic cell harvester. In the last 16 hours of culture, wells were pulsed with $^3$H-thymidine (1 µCi/well), then harvested onto printed glass fibre filters with a 96-well automatic cell harvester. $^3$H-thymidine incorporation was measured by liquid scintillation spectroscopy. Toxicity was assessed in a similar manner, except that, in addition to antigen, cells were co-cultured with 25 U/ml of rIL-2, in the absence of APC.

Harvesting of T Cell Culture Supernatants for Cytokine Testing

Supernatants (70-75 µl/well of triplicate cultures) were harvested and pooled from T cell proliferation assay cultures at 48 hours (IL-5, IFN-γ) and frozen at −80° C. Harvested supernatants were replaced with warm (37° C.) complete medium and cells subsequently pulsed and harvested as described previously.

(i) Flow Cytometry

T cells from in vitro culture were washed once in cold (4° C.) FACS wash buffer prior to staining. Cells (0.5×10$^6$/tube) were stained with appropriate fluorochrome-labelled monoclonal antibodies or relevant isotype controls (10 µl/tube) for 15 minutes on ice and protected from light. Cells were washed once by addition of cold wash buffer, pelleted by centrifugation (329×g 5 minutes, 4° C.) and resuspended in wash buffer. The percentage and mean fluorescence intensity of stained cells was determined from 100,000 events using a Becton Dickinson FACScalibur flow cytometer and "Cell Quest" software.

(j) Cytokine ELISA

IL-5 and IFN-γ levels in culture supernatants were measured by sandwich ELISA. White Costar (Corning, USA) ELISA plates were coated with capture mAb (IL-5 and IFN-γ, 2 µg/ml; 30 µl/well) diluted in binding buffer overnight at 4° C. Plates were then washed three times in PBS/0.05% Tween (wash buffer) and wells blocked with 100 µl/well of 1% BSA/PBS (blocking buffer) for 1 hour at room temperature. Following three washes in wash buffer, 30 µl/well of serial dilutions of recombinant human IL-5 or IFN-γ (5000-0.15 pg/ml) in blocking buffer-0.05% Tween or culture supernatants were added and incubated overnight at 4° C. Following four washes in wash buffer, plates were incubated with biotinylated detection mAb (IL-5, 1 µg/ml; IFN-γ, 0.5 µg/ml; 50 µl/well) diluted in blocking buffer for 1 hour at room temperature. Plates were then washed 6 times in wash buffer and incubated with a 1 in 2000 dilution of streptavidin-peroxidase (50 µl/well) in blocking buffer for 45 minutes at room temperature. Following 8 washes in wash buffer, 100 µl/well of freshly prepared chemiluminescent substrate (Perkin-Elmer, USA) was used and plates read in a Lumicount microplate glow luminometer (Packard Instrument Company, USA), 0.5 seconds/well, automatic sensitivity setting. Standard curve construction and determination of unknown cytokine levels was performed using Packard Instruments software. IL-5 and IFN-γ ELISA sensitivities were 2 pg/ml and 4 pg/ml, respectively.

(k) Statistical Analysis

All statistical analysis was performed using SPSS statistical software (SPSS, USA). For non-normally distributed data, a Mann-Whitney test was employed to assess the level of significance of differences between values for a particular parameter for any two groups. For continuous variables, linear regression analysis (Pearson's) was performed to assess the degree of correlation between two parameters while logistic regression analysis was performed for categorical data.

Example 2

Subject Characterisation

Clinical characteristics of donor subjects used for these experiments are detailed in table 4. A total of 22 peanut allergic subjects were used for Ara h 2 T cell epitope mapping, of whom 15 were female. The average age of subjects was 32 years (range 19-55 years). Nineteen of the 22 subjects suffered from other allergic diseases, including asthma, eczema or allergic rhinitis. Of the 19 subjects for whom skin prick testing had been performed, only one was non-atopic. Each subject described typical features of anaphylaxis on exposure to peanut, beginning within minutes of that exposure. Laryngeal oedema was the most common symptom, with 17 of the 22 subjects describing this symptom at the time of anaphylaxis. Other common symptoms were asthma, generalised urticaria, and facial angioedema. Five of the 22 subjects reported anaphylaxis occurring only on exposure to peanut, but only one of those five was also RAST test negative to all other nuts tested. RAST testing data showed no correlation to the severity of reactions subjects experienced with exposure to peanut.

Peanut Allergen Preparation

Figure 2:
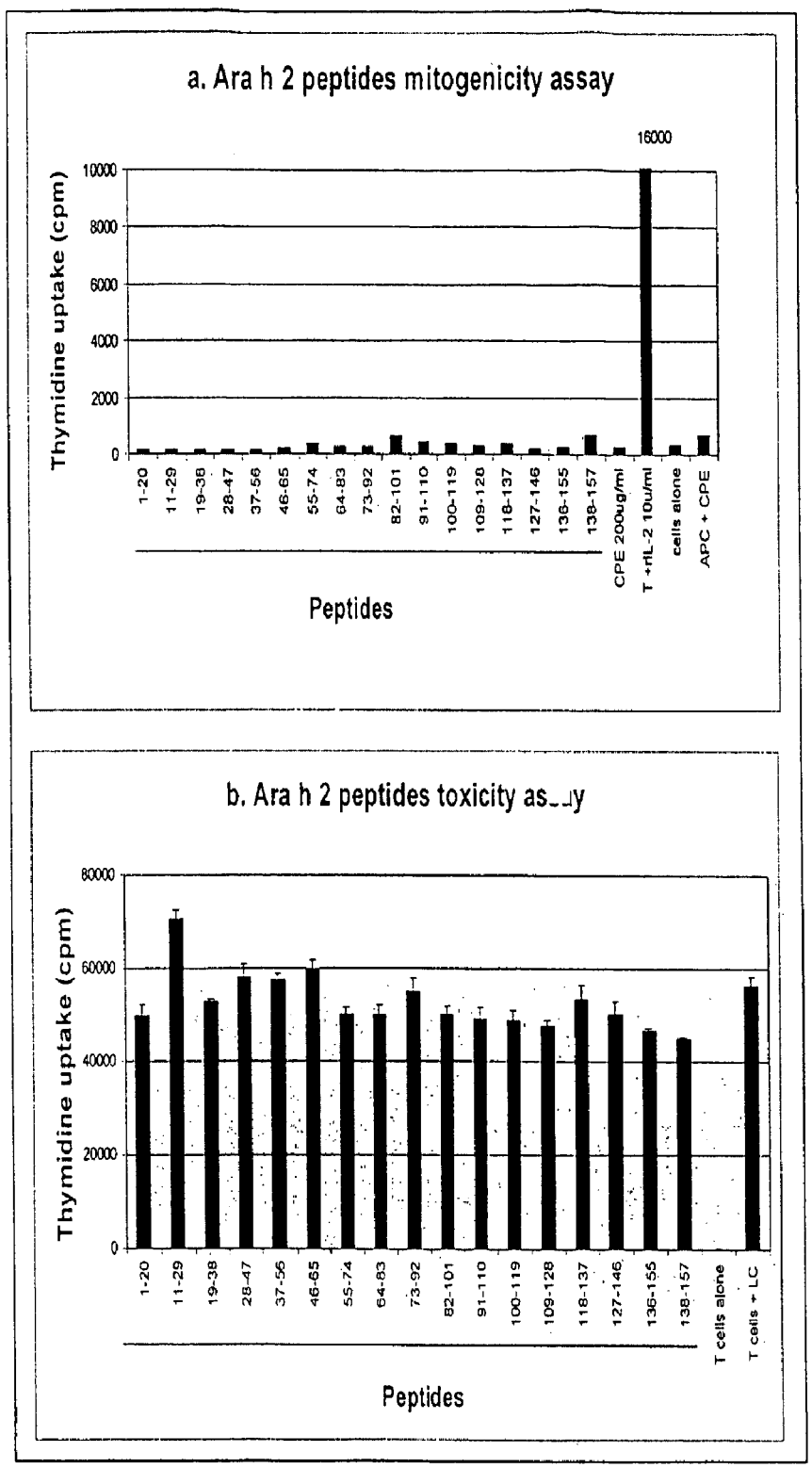
FIG. 2 is a graphical representation of the evaluation of T cell mitogenic and cytotoxic potential of Ara h 2 dodecapeptides.

The manufacture and characterisation of CPE and recombinant Ara h 2 is described in Example 1. The sequences of the Ara h 2 peptides used for epitope mapping are illustrated in FIG. 1 (Chiron Mimitopes, Australia). Each peptide was 20 amino acids in length with an 11 amino acid shared sequence with adjacent peptides, except for that closest to the N-terminus, where the matching sequence was 18 amino acids in length. Characterisation of peptides with regards T cell mitogenicity and toxicity is displayed in FIG. 2, and demonstrates that all peptides were free of these potential confounders.

Western Blotting of Ara h 2

To determine the frequency of Ara h 2 IgE reactivity amongst the study cohort, western blotting of CPE was carried out. These results are shown in FIG. 3 and demonstrate that 20 out of the 22 peanut allergic subjects possessed IgE reactive to a doublet of approximately 14 kDa, representing Ara h 2. Interestingly, apart from Ara h 2, 19 of the 22 subjects recognised a band of approximately 11 kDa, likely to represent either Ara h 3, Ara h 5 or Ara h 6. Non-peanut allergic controls also showed binding to Ara h 2 and the 11 kDa protein, but this was weak and potentially non-specific in this highly sensitive assay.

Polyclonal T Cell Responses to Crude Peanut Extract

To ensure that CPE-specific T cells were present within the study subjects' T cell repertoire, PBMC proliferative responses to stimulation with CPE were analysed, demonstrating a dose response for both peanut allergic subjects and non-peanut allergic controls. For each subject, the lowest dose that produced maximal stimulation at 7 days was used to drive peanut specific T cell lines for use in peptide assays, and ranged between 50 and 200 µg/ml.

Mapping of Ara h 2 T Cell Epitopes

To determine the T cell epitopes of Ara h 2, oligoclonal CPE-specific TCL were generated from PBMC of 21 peanut-allergic donors and 5 non-peanut allergic donors, and stimulated with a nested set of synthetic peptides spanning the entire Ara h 2 sequence (FIG. 1). A peptide concentration of 10 µg/ml was determined to be the optimal stimulating concentration within proliferation assays. Optimisation included assays at both 10 µg/ml and 30 µg/ml. Responses to each concentration proved similar, although some subjects who did not respond significantly to any peptide at a concentration of 10 µg/ml demonstrated an indiscriminate low grade response to most peptides at the higher concentrations, that did not provide any differential signal. In this setting, and because of the limited availability of donor cells and the cost of commercially prepared peptides, the lower concentration was used.

Several approaches to the production of TCL were used, including stimulation of cells with two and three pulses of CPE separated by 7 days each, two pulses of CPE with a third pulse of rAra h 2, again separated by 7 days each, and three stimulations with rAra h 2. Responses by TCL receiving two CPE stimulations were in general lower than those receiving three stimulations, such that it was felt the sensitivity of the assay may be compromised. Responses of TCL receiving a third pulse with rAra h 2 were surprisingly infrequent on the basis of the frequent sensitivity demonstrated to Ara h 2 by western blotting, while responses by cells receiving three pulses with rAra h 2 were universally absent, suggesting that the rAra h 2 extract may have contained other antigens or substances blunting the T cell response to the allergen. This lead to the use of TCL stimulated with 3 pulses of CPE, each separated by 7 days for all subjects tested. Data from subjects demonstrating a peptide response to two pulses of CPE and a final pulse of rAra h 2 are also presented.

Individual responses to peptide, Ara h 2 and CPE are demonstrated in FIGS. 4 and 5 and summarised in table 5. A total of 9 (41%) of the 22 peanut allergic subjects demonstrated a proliferative response to one or more of the Ara h 2 peptides, with 8 subjects responding using CPE driven TCL, two subjects responding using both methods of TCL generation, and one subject responding only when using a TCL driven with a pulse of rAra h 2. Of interest, PBMC from non-peanut allergic subjects could not be used to generate a TCL, cells becoming non-viable after two stimulations or demonstrating a non-discriminatory "high background" response to all antigens assayed. CPE specific TCL could be generated from 19 (86%) of the 22 peanut allergic subjects, with 6 (32%) of those 19 peanut specific TCL responding to rAra h 2. Proliferative responses to rAra h 2 showed best correlation with responses to Ara h 2 (19-38) and Ara h 2 (28-47), in that where a subject had a response to these peptides, 60% also had a proliferative response to Ara h 2. No other peptides were as clearly associated with a response to rAra h 2. Only 2 peptide non-responsive TCL demonstrated a proliferative response to rAra h 2. No subject without specific IgE towards Ara h 2 demonstrated a proliferative response to peptide, but the intensity of IgE reactivity could not otherwise be used to predict a peptide response.

Using CPE driven TCL, of the 17 peptides tested, 7 (41%) induced a proliferative response. Ara h 2 (19-38) and Ara h 2 (73-92) were associated with the greatest frequency of response, producing proliferative responses in 3 of the 8 responders. Other peptides inducing proliferative responses were located at Ara h 2 (28-47), Ara h 2 (55-74), Ara h 2 (82-101), Ara h 2 (91-110), Ara h 2 (100-119), and Ara h 2 (136-155). No peptide was associated with a response in over 25% of the 22 CPE driven TCL. Only 2 peptides produced responses in greater than 25% of CPE driven TCL that demonstrated a peptide response, these being Ara h 2 (19-38) and Ara h 2 (73-92). Comparison of the magnitude of response to each antigen demonstrates a great variation between subjects. When response magnitude was ranked for each subject, the greatest responses were towards Ara h 2 (19-38), with 3 subjects demonstrating their greatest response to this peptide.

Peptide responses by rAra h 2 pulsed TCL occurred in 3 of 20 TCL generated in this fashion. Peptide responses were widespread amongst those responders, and only two peptides, Ara h 2 (64-83) and Ara h 2 (109-128) did not produce a response in at least one subject. The magnitude of responses towards peptides by these TCL was greater than that demonstrated by CPE driven TCL, the greatest response being by subject 10 towards Ara h 2 (37-56), where the stimulation index was 30.3. Comparison of peptide responses demonstrated by the different types of TCL revealed some common peptide responses, but several differences. Only two subjects demonstrated significant peptide responses to both methods of TCL preparation. Subject 10 reacted to Ara h 2 (19-38) using both types of TCL preparation, but the magnitude of the response to this peptide in the rAra h 2 pulsed TCL was less than that generated by stimulation with Ara h 2 (37-56) and Ara h 2 (46-65). The pattern of reactivity demonstrated by subject 6 was similar for both types of TCL, but did not include Ara h 2 (73-92) or Ara h 2 (136-155) for rAra h 2 pulsed TCL.

Cytokine Responses to Peptides Associated with a Proliferative Response

To identify the phenotype of T cells associated with a peptide proliferative response, supernatants were collected from TCL cultures 48 hours after stimulation with peptides and assayed for the presence of IL-5 and IFN-γ. For each donor, peptides associated with a proliferative response and two peptides not associated with a proliferative response were tested. Of the 8 CPE driven TCL examined, 7 demonstrated detectable cytokine levels. Individual cytokine ratios for CPE driven TCL are demonstrated in FIG. 5.8. The magnitude of cytokine responses associated with individual peptides varied greatly between subjects, from the lower limits of detection for both cytokines, up to 2054 pg/ml for IL-5, and 2966 pg/ml for IFN-γ. In general, cytokine responses were at the lower limits of detection. The greatest individual IL-5 response was to Ara h 2 (19-38) with subject 21 producing 2054 pg/ml of IL-5 and subject 10 producing 540 pg/ml of IL-5 towards this peptide. These responses were substantially greater than the next largest cytokine response demonstrated by other subjects.

IL-5/IFNγ ratios were skewed towards greater IL-5 production, for peptide responses in 5 of the 7 subjects whose CPE driven TCL demonstrated a proliferative response. The greatest ratio occurred towards Ara h 2 (19-38), being approximately 20 for subject 21, and 7 in subject 10. Only these subjects demonstrated an IL-5/IFN-γ ratio of greater than 1 for rAra h 2 and CPE. For peptides not associated with a proliferative response, the IL-5/IFN-γ ratio was less than 1 for 5 out of 7 subjects.

Cytokine responses by rAra h 2 pulsed TCL could only be demonstrated in two of the three demonstrating a proliferative response to peptides and are illustrated in FIG. 5.8. The response of these TCL was predominantly characterised by IFN-γ production (data not shown), again suggesting that rAra h 2 pulsed TCL were of a different phenotype to CPE generated TCL, and may have been contaminated with either different antigens or other immunomodulatory substances. IL-5 production could only be detected in low levels or not at all for peptides not associated with a proliferative response, but was clearly detectable for those producing proliferation. This is in contrast to IFN-γ, for which detectable levels occurred for all peptides, although at increased levels for those peptides producing a proliferative response.

Example 3

Site-Directed Mutagenesis of ARA H 2

Site directed mutagenesis of a Ara h 2 construct is carried out using the QuickChange™XL site direct mutagenesis kit (Stratagene, Calif., USA) according to the manufacturer's instructions. Primers are used to replace one or more cysteine amino acids with an alanine. After site-directed mutagenesis the construct is sequenced to confirm the nucleotide changes. The construct containing the mutant Ara h 2 is transformed into *E. coli* strain BL21-CodonPlus® (DE3)-RIL competent cells, expressed and purified as above. This technique can be correspondingly applied to the mutation of any other type of amino acid.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4

Clinical features of the 22 peanut allergic subjects used for T cell Ara h 2 epitope mapping

| Subject | Sex | Age | Allergic disease | Clinical features | Known nut allergens | Other food allergens | Age at first reaction (yrs) | Time since last reaction (mths) | level | score | Atopic status |
|---|---|---|---|---|---|---|---|---|---|---|---|
| 1 | F | 27 | asthma, rhinitis, eczema | laryngeal oedema, urticaria, facial angioedema | peanut, hazelnut, walnut | sesame seed, baked beans | 10 | 2 | 2.07 | 2 | GP, B, HDM, C, A |
| 2 | F | 34 | asthma | asthma, laryngeal oedema, urticaria, facial angioedema | peanut | peas, lentils | 14 | 192 | 0.73 | 2 | GP, B, HDM |
| 3 | F | 40 | asthma, eczema | asthma, laryngeal oedema, loss of consciousness, urticaria, facial angioedema | peanut, Brazil nut, cashew nut, hazelnut | nil | 2 | 12 | 3.61 | 3 | C |
| 4 | M | 27 | rhinitis | asthma, laryngeal oedema, urticaria | peanut, almond, brazilnut, hazelnut, macadamia, walnut | pine nuts, citrus seeds | 2 | 4 | mixed nut RAST: 3/4 | | |
| 5 | F | 31 | rhinitis, eczema | GIT upset, asthma, laryngeal oedema, urticaria | peanut, almond, hazelnut, pistachio | | 1.5 | 18 | 13.6 | 3 | GP, HDM, C |
| 6 | F | 33 | nil | GIT upset, urticaria | peanut, hazelnut | pine nuts | 0.5 | 3 | 13.3 | 3 | GP, B, HDM, C |
| 7 | F | 27 | eczema | asthma, laryngeal oedema, urticaria, angioedema | peanut, almond | | 19 | 11 | 9.53 | 3 | |
| 8 | F | 19 | asthma | laryngeal oedema, urticaria | peanut, almond, Brazil nut, cashew, | crustacea | 3 | 12 | 3.09 | 2 | GP, HDM, C |

TABLE 4-continued

Clinical features of the 22 peanut allergic subjects used for T cell Ara h 2 epitope mapping

| Subject | Sex | Age | Allergic disease | Clinical features | Known nut allergens | Other food allergens | Age at first reaction (yrs) | Peanut RAST Time since last reaction (mths) | level | score | Atopic status |
|---|---|---|---|---|---|---|---|---|---|---|---|
| 9 | M | 29 | asthma, rhinitis, eczema | GIT upset, laryngeal oedema, facial angioedema | hazelnut, walnut peanut, almond, Brazil nut, cashew, hazelnut, walnut | pine nuts | 1.5 | 36 | 1.22 | 2 | GP, B, HDM, C |
| 10 | F | 49 | nil | GIT upset, asthma, laryngeal oedema, loss of consciousness, urticaria | peanut, cashew nut | peas | 2 | 18 | 17.6 | 4 | GP |
| 11 | M | 30 | asthma | GIT upset, asthma, laryngeal oedema, facial angioedema | peanut, hazelnut | | 12 | 18 | 0.51 | 1 | |
| 12 | F | 22 | asthma | laryngeal oedema, urticaria, facial angioedema | peanut | | 0.5 | 24 | 16.3 | 3 | GP, HDM |
| 13 | F | 36 | asthma, eczema | GIT upset, asthma, hypotension, facial angioedema | peanut, hazelnut | | 4 | 2 | 3.09 | 2 | GP, HDM, C |
| 14 | F | 50 | nil | laryngeal oedema, urticaria, facial angioedema | peanut | | 18.5 | 21 | 6.87 | 3 | GP, HDM, C |
| 15 | M | 27 | asthma, rhinitis | asthma, laryngeal oedema, urticaria, facial angioedema | peanut, almond, hazelnut | avocado | 1.5 | 24 | 12.4 | 3 | GP, B, HDM |
| 16 | F | 37 | rhinitis, eczema | GIT upset, asthma, laryngeal oedema, hypotension | peanut, hazelnut | pine nuts | 10 | 36 | 0 | 0 | GP, HDM, peanut 14 mm |
| 17 | M | 35 | asthma, rhinitis, eczema | asthma, urticaria, facial angioedema | peanut, hazelnut | | 8 | 12 | 2.82 | 2 | |
| 18 | F | 22 | rhinitis | GIT upset, asthma, laryngeal oedema, facial angioedema | peanut, hazelnut, pistachio | | 8 | 9 | 0.39 | 1 | GP |
| 19 | M | 55 | asthma, eczema | asthma, laryngeal oedema, facial angioedema | peanut, walnut | banana | 1.5 | 120 | 2.01 | 2 | GP, HDM, A |
| 20 | F | 30 | asthma | asthma, uticaria, laryngeal oedema, facial angioedema | peanut, Brazil nut, almond | | 3 | 228 | | 0 | |
| 21 | M | 28 | asthma | GIT upset, laryngeal oedema, urticaria | peanut, hazelnut, egg, milk | | 5 | 1 | 100 | 6 | HDM |
| 22 | F | 32 | asthma, eczema | asthma, urticaria, facial angioedema | peanut, | | 0 | 0 | | 0 | |

Legend:
GP, grass pollen;
B, birch;
HDM, house dust mite;
C, cat;
A, alternaria

TABLE 5

Summary of TCL proliferative responses to Ara h 2 peptides, rAra h 2, and CPE

| | 1-20 | 10-29 | 19-38 | 28-47 | 37-56 | 46-65 | 55-74 | 64-83 | 73-92 | 82-101 | 91-110 | 100-119 | 109-128 | 118-137 | 127-146 | 136-155 | 138-157 | Ara h 2 | CPE |
|---|---|---|---|---|---|---|---|---|---|---|---|---|---|---|---|---|---|---|---|
| CPE driven lines | | | | | | | | | | | | | | | | | | | |
| Subject 21 | 0.9 | 1.0 | 26.8 | 1.3 | 0.7 | 0.9 | 1.9 | 1.0 | 1.1 | 1.1 | 1.3 | 1.3 | 1.0 | 0.9 | 0.9 | 1.0 | 2.0 | 20.9 | 89.9 |
| Subject 13 | 2.4 | 0.8 | 5.2 | 0.8 | 0.7 | 0.6 | 0.8 | 0.7 | 0.4 | 0.6 | 0.6 | 0.7 | 1.2 | 0.8 | 0.9 | 0.8 | 0.7 | 2.3 | 4.8 |
| Subject 10 | 1.5 | 1.1 | 3.1 | 1.3 | 1.7 | 1.6 | 1.4 | 0.8 | 1.5 | 0.8 | 1.5 | 1.1 | 1.0 | 1.5 | 2.2 | 1.0 | 1.2 | 5.8 | 52.0 |
| Subject 6 | 1.1 | 1.5 | 1.5 | 2.8 | 0.9 | 2.3 | 1.2 | 2.1 | 3.3 | 2.4 | 5.3 | 2.9 | 1.6 | 1.2 | 2.6 | 2.9 | 5.7 | 34.2 |
| Subject 19 | 0.9 | 1.1 | 2.3 | 2.6 | 1.7 | 1.7 | 2.2 | 1.9 | 1.8 | 2.3 | 1.7 | 1.7 | 1.4 | 1.4 | 1.8 | 1.6 | 0.9 | 0.8 | 4.4 |
| Subject 17 | 2.3 | 1.1 | 1.6 | 1.8 | 1.1 | 1.1 | 1.6 | 1.9 | 6.7 | 1.5 | 1.1 | 2.5 | 1.0 | 1.3 | 1.2 | 1.1 | 1.1 | 1.4 | 13.9 |
| Subject 16 | 1.3 | 1.8 | 1.9 | 1.3 | 1.7 | 2.1 | 2.7 | 1.5 | 2.7 | 1.9 | 2.2 | 2.1 | 1.4 | 1.7 | 1.6 | 1.3 | 1.5 | 1.2 | 3.2 |
| Subject 20 | 1.1 | 1.4 | 1.2 | 1.4 | 1.2 | 1.1 | 1.1 | 1.2 | 1.3 | 2.9 | 2.4 | 1.2 | 1.6 | 1.7 | 1.5 | 1.4 | 1.4 | 1.2 | 15.7 |
| rAra h 2 pulse | | | | | | | | | | | | | | | | | | | |
| Subject 10 | 1.7 | 2.8 | 16.7 | 7.9 | 30.3 | 21.0 | 5.3 | 1.8 | 2.8 | 2.3 | 6.4 | 2.5 | 2.1 | 7.2 | 9.8 | 3.2 | 1.4 | 16.6 | 7.8 |
| Subject 6 | 1.0 | 1.1 | 1.0 | 2.6 | 3.0 | 7.7 | 0.9 | 1.1 | 1.2 | 2.5 | 6.4 | 1.4 | 1.4 | 1.4 | 1.6 | 2.0 | 6.2 | 20.1 |
| Subject 15 | 2.7 | 2.4 | 4.3 | 1.5 | 4.8 | 3.9 | 3.3 | 2.4 | 3.1 | 3.4 | 3.2 | 2.3 | 2.4 | 2.8 | 3.1 | 2.8 | 3.1 | 4.5 | 7.1 |
| Total responders | 11 | 11 | 11 | 11 | 11 | 11 | 11 | 11 | 11 | 11 | 11 | 11 | 11 | 11 | 11 | 11 | 11 | 11 | 11 |
| Peptide response (SI ≥ 2.5) | 1 | 1 | 5 | 4 | 3 | 3 | 3 | 0 | 5 | 2 | 3 | 4 | 0 | 2 | 2 | 3 | 1 | 6 | 11 |
| Percentage total | 9.1 | 9.1 | 45.5 | 36.4 | 27.3 | 27.3 | 27.3 | 0.0 | 45.5 | 18.2 | 27.3 | 36.4 | 0.0 | 18.2 | 18.2 | 27.3 | 9.1 | 54.5 | 100.0 |

BIBLIOGRAPHY

Akdis, C. A. and Blaser, K. (2000). "Mechanisms of allergen-specific immunotherapy." *Allergy* 55: 522-530.

Akdis, C. A. and Blaser, K. (2001). "Bypassing IgE and targeting T cells for specific immunotherapy of allergy." *Trends Immunol* 22: 175-8.

Amann et al., 1998, *Gene.,* 69:301-315

Balderi et al., 1987, *Embo J.,* 6:229-234

Burks, A. W., Williams, L. W., Thresher, W., Connaughton, C., Cockrell, G. and Helm, R. M. (1992). "Allergenicity of peanut and soybean extracts altered by chemical or thermal denaturation in patients with atopic dermatitis and positive food challenges." *Int Arch Allergy Immunol.* 119: 165-172.

Burks, W., Sampson, H. A. and Bannon, G. A. (1998). "Peanut allergens." *Allergy* 53: 725-30.

Clarke, M. C., Kilburn, S. A., Hourihane, J. O., Dean, K. R., Warner, J. O. and Dean, T. P. (1998). "Serological characteristics of peanut allergy." *Clin Exp Allergy* 28: 1251-7.

de Jong, E. C., Van Zijverden, M., Spanhaak, S., Koppelman, S. J., Pellegrom, H. and Penninks, A. H. (1998). "Identification and partial characterization of multiple major allergens in peanut proteins." *Clin Exp Allergy* 28: 743-51.

Hourihane, J. B., Kilburn, S. A., Nordlee, J. A., Hefle, S. L., Taylor, S. L. and Warner, J. O. (1997). "An evaluation of the sensitivity of subjects with peanut allergy to very low doses of peanut protein: a randomized, double-blind, placebo-controlled food challenge study." *J Allergy Clin Immunol* 100: 596-600.

Jameel et al., 1990, *J. Virol.,* 64:3963-3966

Kleber-Janke, T., Crameri, R., Appenzeller, U., Schlaak, M. and Becker, W. M. (1999). "Selective cloning of peanut allergens, including profilin and 2S albumins, by phage display technology." *Int Arch Allergy Immunol* 119: 265-274.

Knapp et al., 1990, *Bio Techniques.,* 8:280-281

Kurjan and Herskowitz., 1982, *Cell.,* 30.933-943

Litwin, A., Pesce, A. J. and Michael, J. G. (1988). "Regulation of the immune response to allergens by immunosuppressive allergenic fragments. 1. Peptic fragments of honey bee venom phospholipase A2." *Int Arch Allergy Appl Immunol* 87: 361-6.

Maguire, P., Nicodemus, C., Robinson, D., Aaronson, D. and Umetsu, D. T. (1999). "The safety and efficacy of ALLERVAX CAT in cat allergic patients." *Clin Immunol* 93: 222-31.

Marcotte, G. V., Braun, C. M., Norman, P. S., Nicodemus, C. F., Kagey-Sobotka, A., Lichtenstein, L. M. and Essayan, D. M. (1998). "Effects of peptide therapy on ex vivo T-cell responses." *J Allergy Clin Immunol* 101: 506-13.

Muller, U., Akdis, C. A., Frickler, M., Akdis, M., Blesken, T., Betens, F. and Blaser, K. (1998). "Successful immunotherapy with T-cell epitope peptides of bee venom phospholipase A2 induces specific T-cell anergy in patients allergic to bee venom." *J Allergy Clin Immunol.* 101: 747-754.

Nelson, H. S., Lahr, J., Rule, R., Bock, A. and Leung, D. (1997). "Treatment of anaphylactic sensitivity to peanuts by immunotherapy with injections of aqueous peanut extract." *J Allergy Clin Immunol* 99: 744-51.

Norman, P. S., Ohman, J. L., Jr., Long, A. A., Creticos, P. S., Gefter, M. A., Shaked, Z., Wood, R. A., Eggleston, P. A., Hafner, K. B., Rao, P., Lichtenstein, L. M., Jones, N. H. and Nicodemus, C. F. (1996). "Treatment of cat allergy with T-cell reactive peptides." *Am J Respir Crit Care Med* 154: 1623-8.

Oppenheimer, J. J., Nelson, H. S., Bock, S. A., Christensen, F. and Leung, D. Y. (1992). "Treatment of peanut allergy with rush immunotherapy [see comments]." *J Allergy Clin Immunol* 90: 256-62.

Pene, J., Desroches, A., Paradis, L., Lebel, B., Farce, M., Nicodemus, C. F., Yssel, H. and Bousquet, J. (1998). "Immunotherapy with Fel d 1 peptides decreases IL-4 release by peripheral blood T cells of patients allergic to cats." *J Allergy Clin Immunol* 102: 571-8.

Primeau, M. N., Kagan, R., Joseph, L., Lim, H., Dufresne, C., Duffy, C., Prhcal, D. and Clarke, A. (2000). "The psychological burden of peanut allergy as perceived by adults with peanut allergy and the parents of peanut-allergic children." *Clin Exp Allergy* 30: 1135-43.

Robinson, D. S. (2000). "Th-2 cytokines in allergic disease." *Br Med Bull* 56: 956-968.

Sambruck et al., 1989, Cold Spring Harbour Laboratory Press; Cold Spring Harbour, N.Y Sampson, H. A., Mendelson, L. and Rosen, J. P. (1992). "Fatal and near-fatal anaphylactic reactions to food in children and adolescents." *N Engl J Med* 327: 380-4.

Schultz et al., 1987, *Gene.,* 54:113-123

Sicher, S. H., Munoz-Furlong, A., Burks, A. W. and Sampson, H. A. (1999) "Prevalence of peanut and tree nut allergy in the US determined by random digital telephone survey." *J Allergy Clin Immunol* 103: 559-562.

Sicherer, S. H., Burks, A. W. and Sampson, H. A. (1998). "Clinical features of acute allergic reactions to peanut and tree nuts in children." *Paediatrics* 102: e6.

Stanley, J. S., King, N., Burks, A. W., Huang, S. K., Sampson, H., Cockrell, G., Helm, R. M., West, C. M. and Bannon, G. A. (1997). "Identification and mutational analysis of the immunodominant IgE binding epitopes of the major peanut allergen Ara h 2." *Arch Biochem Biophys.* 342: 244-253.

Varney et al. 1991 *British Medical Journal* 302:265-269.

---

The claims defining the invention are as follows:

1. An isolated peptide comprising an Ara h 2 T cell epitope said peptide consisting of 16 to 20 contiguous amino acids of an amino acid sequence selected from:
   (i) amino acids 28-47 of Ara h 2 (RRCQSQLERANLR-PCEQHLM; SEQ ID NO:5); or
   (ii) amino acids 127-146 of Ara h 2 (KRELRNLPQQCGL-RAPQRCD; SEQ ID NO: 16).

2. A pharmaceutical composition comprising one or more peptides according to claim 1 together with one or more pharmaceutically acceptable carriers and/or diluents.

3. A diagnostic kit for use in a method of diagnosing or monitoring a condition in a mammal, which condition is hypersensitivity to peanuts or tree nuts which contain Ara h 2, wherein said kit comprises a peptide according to claim 1.

* * * * *